United States Patent [19]
Petre et al.

[11] Patent Number: 5,635,391
[45] Date of Patent: Jun. 3, 1997

[54] **ISOLATED DNA ENCODING A NITRILASE POLYPEPTIDE, HOSTS CONTAINING, AND EXPRESSION THEREOF OPTIONALLY ASSISTED BY A *E. COLI* GROE CHAPERONE POLYPEPTIDE**

[75] Inventors: Dominique Petre, Lyons; Edith Cerbeleaud, La Mulatiere; Sophie Levy-Schil; Joël Crouzet, both of Paris, all of France

[73] Assignee: Rhone-Poulenc Chimie, Courbevoie Cedex, France

[21] Appl. No.: 465,615

[22] Filed: Jun. 5, 1995

Related U.S. Application Data

[63] Continuation of Ser. No. 194,588, Feb. 10, 1994, abandoned, which is a continuation-in-part of Ser. No. 102,747, Aug. 6, 1993, abandoned.

[30] Foreign Application Priority Data

Aug. 10, 1992 [FR] France .................... 92 09882

[51] Int. Cl.$^6$ .................... C12N 1/21; C07H 21/04
[52] U.S. Cl. .................... 435/252.3; 435/252.32; 435/252.33; 435/252.34; 536/23.2; 536/23.7
[58] Field of Search .................... 435/252.32, 252.33, 435/252.34; 536/23.2, 23.7

[56] References Cited

U.S. PATENT DOCUMENTS 4,810,648  3/1989  Stalker .................... 435/191

OTHER PUBLICATIONS

Gavini et al, "Genomic and Phenotypic Characterizations . . . " *Curr. Microbiol.* 21:279–282 (1990).
Kobayashi et al, "Nitrilate from *Rhodococcus rhodochrous* J1", *J. Biol. Chem.* 267:20746–20751 (Oct. 1992).
Bartling et al, "Cloning and expression of an *Arabidopsis* nitrilase . . . " *Eur. J. Biochem.* 205:417–424 (Apr. 1992).
Kusukawa et al, "Effects of mutations in heat shock genes groES and groEL . . . " *EMBO J.* 8(11):3517–3521 (1989).
Kobayashi et al, "Nitrilase in biosynthesis of the plant hormone . . . " *PNAS* 90:247–251.

Primary Examiner—Robert A. Wax
Assistant Examiner—Kawai Lau
Attorney, Agent, or Firm—Burns, Doane, Swecker & Mathis, L.L.P.

[57] ABSTRACT

The present invention relates to novel polypeptides having a nitrilase activity and to the genetic tools for producing them, namely:

- the DNA sequence coding for a polypeptide having a nitrilase activity and capable of hydrolyzing nitriles to carboxylates,
- an analog of this sequence resulting from the degeneracy of the genetic code,
- a DNA sequence hybridizing with one of these sequences or a fragment thereof and coding for a polypeptide having a nitrilase activity,
- expression cassettes and microorganisms enabling them to be obtained. Application: enzymatic conversion of nitriles to carboxylates.

18 Claims, 12 Drawing Sheets

FIG.4A

```
ctcgagacaaaattggacagtcgcccctatctgcaaaatggaacctccttgcacatctataaatttt                                    72 tgaggagacagca ATG AAA AAT TAT CCT ACA GTC AAG GTA GCA GCA GTG CAA GCT       128
              Met Lys Asn Tyr Pro Thr Val Lys Val Ala Ala Val Gln Ala       14

GCT CCT GTA TTT ATG AAT CTA GAG GCA ACA GTA GAT AAA ACT TGT AAG TTA ATA     182
Ala Pro Val Phe Met Asn Leu Glu Ala Thr Val Asp Lys Thr Cys Lys Leu Ile      32

GCA GAA GCA GCA TCT ATG GGC GCC AAG GTT ATC GGC TTC CCA GAA GCA TTT ATT     236
Ala Glu Ala Ala Ser Met Gly Ala Lys Val Ile Gly Phe Pro Glu Ala Phe Ile      50

CCC CGC TAT CCA TAT TGG ACA TCA AAT ATG GAC TTC ACT GGA ATG ATG             290
Pro Arg Tyr Pro Tyr Trp Thr Ser Asn Met Asp Phe Thr Gly Met Met              68

TGG GCC GTC CTT TTC AAG AAT GCG ATT GAA ATC CCA AGC AAA GAA GTT CAA CAA     344
Trp Ala Val Leu Phe Lys Asn Ala Ile Glu Ile Pro Ser Lys Glu Val Gln Gln      86

ATT AGT GAT GCT GCA AAA AAG AAT GGA GTT TAC GTT TGC GTT TCT GTA TCA GAG     398
Ile Ser Asp Ala Ala Lys Lys Asn Gly Val Tyr Val Cys Val Ser Val Ser Glu     104

AAA GAT AAT GCC TCG CTA TAT TTG ACG CAA TTG TGG TTT GAC CCG AAT GGT AAT     452
Lys Asp Asn Ala Ser Leu Tyr Leu Thr Gln Leu Trp Phe Asp Pro Asn Gly Asn     122

TTG ATT GGC AAG CAC AGG AAA TTC AAG CCC ACT AGT GAA AGA GCT GTA TGG         506
Leu Ile Gly Lys His Arg Lys Phe Lys Pro Thr Ser Glu Arg Ala Val Trp         140

GGA GAT GGG GAT AGC ATG GCT CCC GTA TTT AAA ACA TTT GGG TAT AAT CTT         560
Gly Asp Gly Asp Ser Met Ala Pro Val Phe Lys Thr Phe Gly Tyr Asn Leu         158

GGG GGA CTC CAG TGC TGG GAA CAT GCT CTC CCA TTA AAC ATT GCG GCG ATG GGC     614
Gly Gly Leu Gln Cys Trp Glu His Ala Leu Pro Leu Asn Ile Ala Ala Met Gly     176
```

FIG. 4B

```
TCA TTG AAC GAA CAG GTA CAT GTT GCT TCC TGG CCA GCC TTC GTC CCT AAA GGC    668
Ser Leu Asn Glu Gln Val His Val Ala Ser Trp Pro Ala Phe Val Pro Lys Gly    194

GCA GTA TCA TCC AGA GTA TCA GTC TGT GCG AAT ACT AGC GCG ATG CAT            722
Ala Val Ser Ser Arg Val Ser Val Cys Ala Asn Thr Ser Ala Met His            212

CAG ATC ATT AGT CAG TTT TAC GCG ATC AGC AAT CAG GTA TAT GTA ATT ATG TCA    776
Gln Ile Ile Ser Gln Phe Tyr Ala Ile Ser Asn Gln Val Tyr Val Ile Met Ser    230

ACC AAT CTC GTT GGC CAA GAC ATG ATT GAC ATG ATT GGG AAA GAT GAA TTT TCC    830
Thr Asn Leu Val Gly Gln Asp Met Ile Asp Met Ile Gly Lys Asp Glu Phe Ser    248

AAA AAC TTT CTA CCG CTT GGT TCT GGA AAC ACA GCG ATT TCT GCA GAG ATT        884
Lys Asn Phe Leu Pro Leu Gly Ser Gly Asn Thr Ala Ile Ser Ala Glu Ile        266

GAG ATT TTG GCA TCA ATT CCA CAA GAC GCG GAG ATT GCT GTT GCC GCC GGT        938
Glu Ile Leu Ala Ser Ile Pro Gln Asp Ala Glu Ile Ala Val Ala Ala Gly        284

GAC CTT AAC CAA ATA ATT TAT GGA AAG TGG TTA CTG GAT CCC GGT CAT TAC        992
Asp Leu Asn Gln Ile Ile Tyr Gly Lys Trp Leu Leu Asp Pro Gly His Tyr        302

TCT ACT CCC GGC TTC TTA AGT TTG ACA TTT GAT CAG TCT GAA CAT GTA CCC GTA    1046
Ser Thr Pro Gly Phe Leu Ser Leu Thr Phe Asp Gln Ser Glu His Val Pro Val    320

AAA AAA ATA GGT GAG CAG ACA AAC CAT TTC ATC TCT TAT GAA GAC TTA CAT GAA    1100
Lys Lys Ile Gly Glu Gln Thr Asn His Phe Ile Ser Tyr Glu Asp Leu His Glu    338

GAT AAA ATG GAT ATG CTA ACG ATT CCG CCG AGG CGC ACA GCC ACA GCG TGA tcgc  1155
Asp Lys Met Asp Met Leu Thr Ile Pro Pro Arg Arg Val Ala Thr Ala           354 cgcctctcggggcgttcggttgctgatagccatcgcctt                                    1194
```

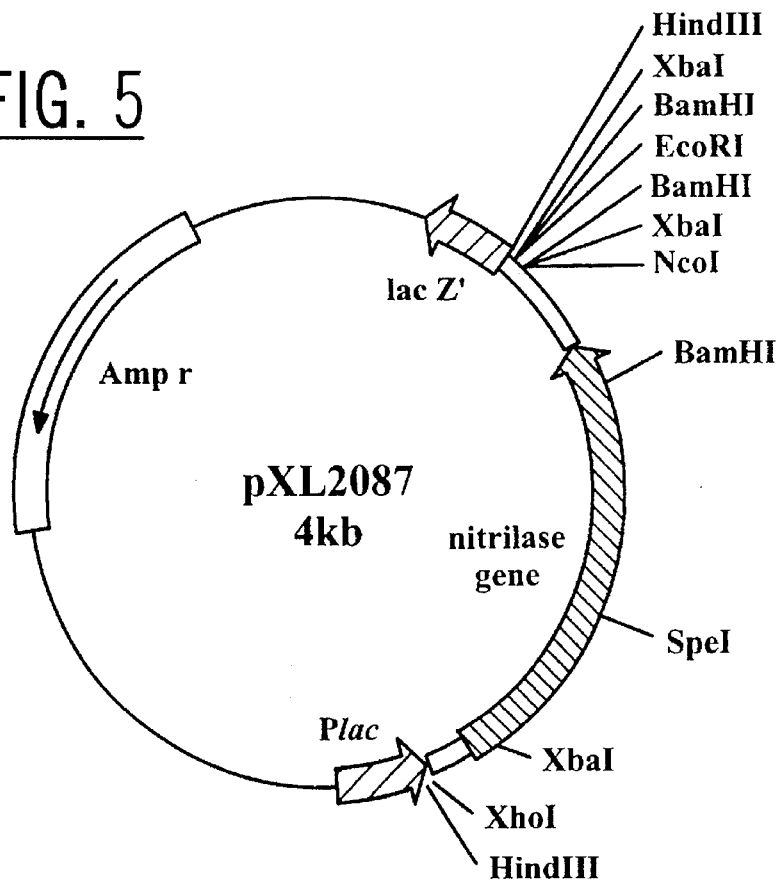
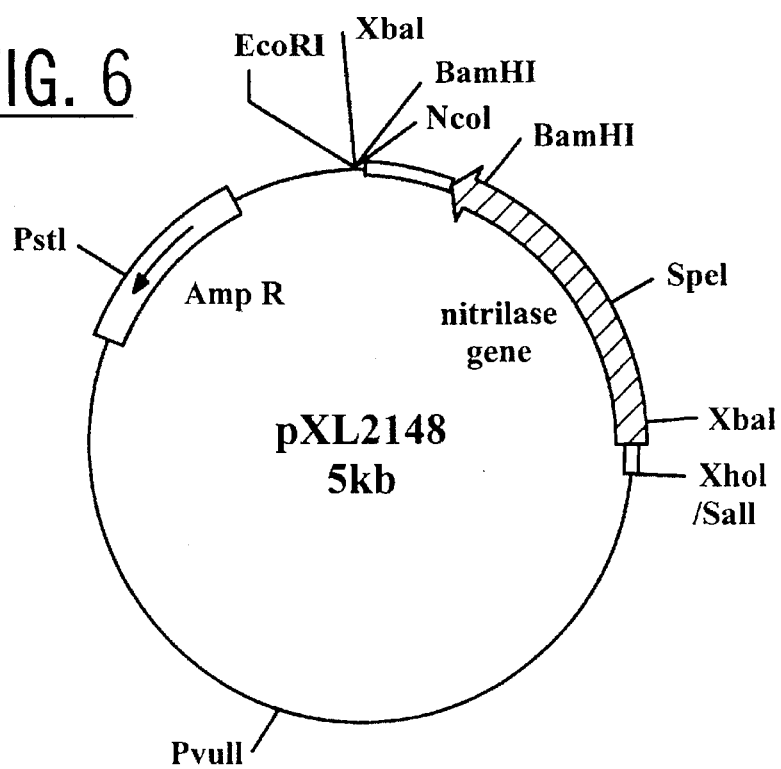

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
Met  Lys  Asn  Tyr  Pro  Thr  Val  Lys  Val  Ala  Ala  Val  Gln  Ala  Ala  Val
 1                   5                        10                       15

Phe  Met  Asn  Leu  Glu  Ala  Thr  Val  Asp  Lys  Thr
                    20                        25
```

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
Met  Lys  Asn  Tyr  Pro  Thr  Val  Lys  Val
 1                   5
```

( 2 ) INFORMATION FOR SEQ ID NO:3:

( i ) SEQUENCE CHARACTERISTICS:
        ( A ) LENGTH: 27 base pairs
        ( B ) TYPE: nucleic acid
        ( C ) STRANDEDNESS: single -continued (D) TOPOLOGY: linear (ii) MOLECULE TYPE: DNA (genomic)

(xi) SEQUENCE DESCRIPTION: SEQ ID NO:3:

ATGAAGAA Y T A Y CCNACNGT NSAAGGT 27

(2) INFORMATION FOR SEQ ID NO:4:

(i) SEQUENCE CHARACTERISTICS:
      (A) LENGTH: 1194 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:4:

| | | | | | |
|---|---|---|---|---|---|
| CTCGAGACAA | AATTGGGACA | GTCGCCCCT | ATCTGCAAAA | TGGAACCTCC | TTTGCACATC | 60 |
| TATAAATTT | TTTGAGGAAG | ACAGCAATGA | AAAATTATCC | TACAGTCAAG | GTAGCAGCAG | 120 |
| TGCAAGCTGC | TCCTGTATTT | ATGAATCTAG | AGGCAACAGT | AGATAAAACT | TGTAAGTTAA | 180 |
| TAGCAGAAGC | AGCATCTATG | GGCGCCAAGG | TTATCGGCTT | CCCAGAAGCA | TTTATTCCCG | 240 |
| GCTATCCATA | TTGGATTTGG | ACATCAAATA | TGGACTTCAC | TGGAATGATG | TGGGCCGTCC | 300 |
| TTTTCAAGAA | TGCGATTGAA | ATCCCAAGCA | AAGAAGTTCA | ACAAATTAGT | GATGCTGCAA | 360 |
| AAAAGAATGG | AGTTTACGTT | TGCGTTTCTG | TATCAGAGAA | AGATAATGCC | TCGCTATATT | 420 |
| TGACGCAATT | GTGGTTTGAC | CCGAATGGTA | ATTTGATTGG | CAAGCACAGG | AAATTTAAGC | 480 |
| CCACTAGTAG | TGAAAGAGCT | GTATGGGGAG | ATGGGGATGG | AAGCATGGCT | CCCGTATTTA | 540 |
| AAACAGAGTA | TGGGAATCTT | GGGGGACTCC | AGTGCTGGGA | ACATGCTCTC | CCATTAAACA | 600 |
| TTGCGGCGAT | GGGCTCATTG | AACGAACAGG | TACATGTTGC | TTCCTGGCCA | GCCTTCGTCC | 660 |
| CTAAAGGCGC | AGTATCATCC | AGAGTATCAT | CCAGCGTCTG | TGCGTCTACT | AATGCGATGC | 720 |
| ATCAGATCAT | TAGTCAGTTT | TACGCGATCA | GCAATCAGGT | ATATGTAATT | ATGTCAACCA | 780 |
| ATCTCGTTGG | CCAAGACATG | ATTGACATGA | TTGGGAAAGA | TGAATTTTCC | AAAAACTTTC | 840 |
| TACCGCTTGG | TTCTGGAAAC | ACAGCGATTA | TTTCTAACAC | CGGTGAGATT | TTGGCATCAA | 900 |
| TTCCACAAGA | CGCGGAGGGA | ATTGCTGTTG | CAGAGATTGA | CCTTAACCAA | ATAATTTATG | 960 |
| GAAAGTGGTT | ACTGGATCCC | GCCGGTCATT | ACTCTACTCC | CGGCTTCTTA | AGTTTGACAT | 1020 |
| TTGATCAGTC | TGAACATGTA | CCCGTAAAAA | AAATAGGTGA | GCAGACAAAC | CATTTCATCT | 1080 |
| CTTATGAAGA | CTTACATGAA | GATAAAATGG | ATATGCTAAC | GATTCCGCCG | AGGCGCGTAG | 1140 |
| CCACAGCGTG | ATCGCCGCCT | CTCGGGGCGT | TCGGTTGCTG | ATAGCCATCG | CCTT | 1194 |

(2) INFORMATION FOR SEQ ID NO:5:

(i) SEQUENCE CHARACTERISTICS:
      (A) LENGTH: 354 amino acids
      (B) TYPE: amino acid
      (D) TOPOLOGY: linear (ii) MOLECULE TYPE: protein (xi) SEQUENCE DESCRIPTION: SEQ ID NO:5:

Met Lys Asn Tyr Pro Thr Val Lys Val Ala Ala Val Gln Ala Ala Pro
1               5                   10                  15

Val Phe Met Asn Leu Glu Ala Thr Val Asp Lys Thr Cys Lys Leu Ile
                20                  25                  30

Ala Glu Ala Ala Ser Met Gly Ala Lys Val Ile Gly Phe Pro Glu Ala

```
                        35                          40                          45
Phe Ile Pro Gly Tyr Pro Tyr Trp Ile Trp Thr Ser Asn Met Asp Phe
    50                      55              60
Thr Gly Met Met Trp Ala Val Leu Phe Lys Asn Ala Ile Glu Ile Pro
65                  70                  75                      80
Ser Lys Glu Val Gln Gln Ile Ser Asp Ala Ala Lys Lys Asn Gly Val
                85              90                      95
Tyr Val Cys Val Ser Val Ser Glu Lys Asp Asn Ala Ser Leu Tyr Leu
            100             105                     110
Thr Gln Leu Trp Phe Asp Pro Asn Gly Asn Leu Ile Gly Lys His Arg
        115                 120                 125
Lys Phe Lys Pro Thr Ser Ser Glu Arg Ala Val Trp Gly Asp Gly Asp
    130                 135                 140
Gly Ser Met Ala Pro Val Phe Lys Thr Glu Tyr Gly Asn Leu Gly Gly
145                 150                 155                     160
Leu Gln Cys Trp Glu His Ala Leu Pro Leu Asn Ile Ala Ala Met Gly
                165                 170                 175
Ser Leu Asn Glu Gln Val His Val Ala Ser Trp Pro Ala Phe Val Pro
            180             185                     190
Lys Gly Ala Val Ser Ser Arg Val Ser Ser Ser Val Cys Ala Ser Thr
        195                 200                 205
Asn Ala Met His Gln Ile Ile Ser Gln Phe Tyr Ala Ile Ser Asn Gln
    210                 215                 220
Val Tyr Val Ile Met Ser Thr Asn Leu Val Gly Gln Asp Met Ile Asp
225                 230                 235                     240
Met Ile Gly Lys Asp Glu Phe Ser Lys Asn Phe Leu Pro Leu Gly Ser
                245                 250                 255
Gly Asn Thr Ala Ile Ile Ser Asn Thr Gly Glu Ile Leu Ala Ser Ile
            260                 265                     270
Pro Gln Asp Ala Glu Gly Ile Ala Val Ala Glu Ile Asp Leu Asn Gln
        275                 280                 285
Ile Ile Tyr Gly Lys Trp Leu Leu Asp Pro Ala Gly His Tyr Ser Thr
    290                 295                 300
Pro Gly Phe Leu Ser Leu Thr Phe Asp Gln Ser Glu His Val Pro Val
305                 310                 315                     320
Lys Lys Ile Gly Glu Gln Thr Asn His Phe Ile Ser Tyr Glu Asp Leu
                325                 330                 335
His Glu Asp Lys Met Asp Met Leu Thr Ile Pro Pro Arg Arg Val Ala
            340                 345                 350
Thr Ala
```

ISOLATED DNA ENCODING A NITRILASE POLYPEPTIDE, HOSTS CONTAINING, AND EXPRESSION THEREOF OPTIONALLY ASSISTED BY A E. COLI GROE CHAPERONE POLYPEPTIDE

This application is a continuation of application Ser. No. 08/194,588, filed Feb. 10, 1994, now abandoned, which is a continuation-in-part of application Ser. No. 08/102,747, Aug. 6, 1993, abandoned.

BACKGROUND OF THE INVENTION

The present invention relates to novel polypeptides having a nitrilase activity and to the genetic engineering tools for producing them, namely a DNA sequence, the expression cassettes carrying this recombinant DNA sequence, and the recombinant microorganisms (host microorganisms) containing said DNA sequence.

The present invention further relates to an enzymatic method of converting nitriles to carboxylates by means of the polypeptides according to the invention or a host microorganism containing the DNA sequence according to the invention.

A first particular application of the method of the invention is the enzymatic synthesis of ammonium adipate or ammonium 5-cyanovalerate by the hydrolysis of adiponitrile with the aid of a polypeptide or host microorganism according to the invention.

Ammonium adipate is known to be a particularly valuable product because it can be converted to adipic acid, a product which is itself widely used for the preparation of nylon 6,6.

The enzymatic hydrolysis of dinitriles has been described by numerous authors. However, the routes by which these dinitriles are hydrolyzed to organic acids are not often referred to. The theoretical hydrolysis scheme is shown in FIG. 12.

In actual fact, it is very often observed that certain routes are preferred and that certain products are not formed or else are not hydrolyzed.

Among the microorganisms for which it has been possible to demonstrate the existence of an enzymatic activity permitting this hydrolysis, there may be mentioned in particular the strains belonging to the genus Fusarium, which degrade succinonitrile and adiponitrile, although the reaction products are not indicated [Goldlust et al., Biotechnol. and Appl. Biochem., 1989, 11, 581]; the strains belonging to the genus Pseudomonas, which degrade adiponitrile [Yanase et al., Agric. Biol. Chem., 1982, 46, 2925]; and the strains belonging to the genus Rhodococcus, in particular *Rhodococcus rhodochrous* NCIB 11 216, which hydrolyzes adiponitrile to adipic acid [Bengis-Garber et al., Appl. Microbiol. Biotechnol., 1989, 32, II], and also *Rhodococcus rhodochrous* K22, whose nitrilase permits the hydrolysis of adiponitrile and glutaronitrile [Yamada et al., J. Bacteriol., 1990, 172 (9), 4807–4815], albeit with a low activity ratio compared with that for the hydrolysis of aromatic nitriles.

Consequently, it can be seen that the enzymatic hydrolysis of dinitriles is rather complex: in all cases, the first CN group is hydrolyzed by the enzyme, while the second group is not hydrolyzed at all in some cases, or else is hydrolyzed at a very low rate in other cases.

SUMMARY OF THE INVENTION

It has now been found that it is possible to hydrolyze nitriles to carboxylates, and more particularly dinitriles to carboxylates or dicarboxylates, totally and rapidly, by using appropriately selected enzymes either as such or, preferably, in the form of recombinant microorganisms which generate them.

A second particular application of the invention is the enzymatic synthesis of ammonium methioninate:

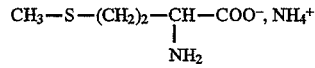

from methiononitrile:

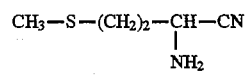

Methionine is one of the only amino acids which is currently produced on a large industrial scale. It constitutes a sulphurized nutriment which is useful, as a growth factor, in feeding animals.

One of its main synthesis chemical routes is the hydrolysis of methiononitrile to ammonium methioninate, using a strong acid. One major drawback of this chemical hydrolysis is that it generates a very high coproduction of salts which are difficult to recycle and which are detrimental to the environment.

The Applicant takes credit for having demonstrated an advantageous enzymatic alternative to the chemical hydrolysis, said alternative solving the problem of detrimental coproduction of salts.

The present invention therefore relates to novel polypeptides having a nitrilase activity which have been isolated from a strain of *Comamonas testosteron*. More precisely, these polypeptides are prepared by extraction and purification from cultures of natural or recombinant microorganisms, the purification being effected by a series of steps consisting in preparing an enzymatic extract from the cell culture, precipitating this extract with ammonium sulfate and purifying it by different steps involving chromatography and gel filtration. These steps, which employ techniques well known to those skilled in the art, are described in detail in the illustrative Examples below.

In the present description, "nitrilase activity" denotes the direct conversion of a nitrile to an ammonium carboxylate, the corresponding amide not being a substrate for the enzyme.

The invention further relates to a DNA sequence coding for a polypeptide having a nitrilase activity. The DNA sequence coding for a polypeptide of the invention can be selected from:

- the DNA sequence coding for a polypeptide having a nitrilase activity, as shown in FIG. 4A and 4B and designated by SEQ ID NO: 4: in the enclosed sequence listing,
- an analog of this sequence resulting from the degeneracy of the genetic code,
- or else a DNA sequence hybridizing with one of these sequences or with a fragment thereof and coding for a polypeptide having a nitrilase activity.

Such a DNA sequence can be obtained by cloning the genomic DNA fragment coding for the desired polypeptide, with the aid of nucleotide probes produced from the purified polypeptide.

The invention further relates to the expression cassettes which carry the above-defined recombinant DNA sequence together with the signals ensuring its expression. These expression cassettes can either be integrated in the genome of the host or located on an expression vector such as a plasmid containing a selection means.

In particular, these expression cassettes contain transcription and translation initiation regions which contain a ribosome binding site and a promoter sequence. These regions may be homologous or heterologous with the microorganism which naturally produces the polypeptide.

The choice of these regions depends especially on the host used. In particular, when the host microorganisms are procaryotic, the heterologous promoter can be selected from strong bacterial promoters such as the tryptophan operon promoter Ptrp of E. coli, the lactose operon promoter Plac of E. coli, the phage lambda right promoter $P_R$, the phage lambda left promoter $P_L$, the strong promoters of Pseudomonas and Comamonas and the strong promoters of Corynebacteria.

More particularly, in the case of the phage lambda right promoter, the thermosensitive form $P_R$CIts may be preferred. In the case of eucaryotic microorganisms such as yeasts, the promoters can originate from glycolytic yeast genes such as the genes coding for phosphoglycerate kinase (PGK), glyceraldehyde-3-phosphate dehydrogenase (GPD), lactase (LAC4) and enolase (ENO).

As far as the ribosome binding sites are concerned, the one derived from the lambda CII gene, as well as those derived from homologous genes of Comamonas or Pseudomonas or those derived from genes of Corynebacteria, are used preferentially when the host microorganism is procaryotic.

A region permitting a termination of the translation and functional transcription of the envisaged host can be positioned at the 3' end of the coding sequence. The expression cassette also comprises one or more markers making it possible to select the recombinant host. The preferred markers are dominant markers, i.e. those conferring a resistance to antibiotics such as ampicillin or streptomycin, or to other toxic products.

Enterobacteria such as E. coli, bacteria belonging to the genera Comamonas or Pseudomonas, and corynebacteria such as those belonging to the genera Corynebacterium, Brevibacterium or Rhodococcus, may be mentioned in particular among the host microorganisms used.

The invention further relates to the microorganisms containing the recombinant DNA sequence according to the invention, for example on a plasmid containing a selection means.

A recombinant microorganism containing said DNA sequence on a plasmid structure was deposited in the Collection Nationale de Cultures de Micro-organismes (C.N.C.M.) (Institut Pasteur, 25 rue du Docteur Roux, Paris) under no. I-1242 on 21st Jul. 1992. This microorganism is the strain E. coli TG1, which contains plasmid pXL2148; this microorganism is also identified by the Applicant using the reference G4207.

The invention further relates to the microorganisms capable of converting nitriles to carboxylates, and more particularly aliphatic dinitriles of the formula NC—R—CN, in which R is a linear or branched alkylene group having from 1 to 10 carbon atoms, to carboxylates, or else aliphatic sulphurized mononitriles such as methiononitriles.

Beyond acquiring their structures I and II during their synthesis by the microorganisms according to the invention, it is important that the polypeptides in question stabilize in their structures III and IV so as to possess an optimal nitrilase activity.

The Applicant takes credit for having discovered means for favoring the above-mentioned stabilization.

Thus any microorganism according to the invention preferably contains:

at least one protein agent for assisting the folding of the polypeptides which the microorganism synthesizes, and in particular the nitrilase referred to in the present disclosure, and/or the genes coding for such an agent, this agent being present in a greater amount than that corresponding to the base level of the microorganism in question.

In terms of the present invention, base level is understood as meaning the maximum level which can be attained by the corresponding wild-type microorganism in question.

Advantageously, this agent is the GroE chaperone of E. coli or its homolog of eucaryotic or procaryotic origin.

The GroE chaperone of E. coli is normally present in the wild-type strains.

The genes coding for the agent are carded by the chromosome or by an extrachromosomal element (plasmid, phage). They are preferably amplified by any known and appropriate means so as to favor the synthesis of the agent in the microorganism.

The genes coding for the agent are under the dependence of expression systems homologous or heterologous with their host microorganism.

The invention further relates to the method of converting nitriles to carboxylates with the aid of a polypeptide according to the invention or a recombinant microorganism which generates it. This method consists in bringing the nitrile to be converted into contact with a polypeptide or recombinant microorganism as defined above. The process is generally carried out at room temperature. In one particular embodiment of the invention, the polypeptide or recombinant microorganism is immobilized on or in a solid support.

The method of the invention is suitable for the conversion of nitriles to carboxylates and more particularly for the conversion to carboxylates, on the one hand, of dinitriles of the formula NC—R—CN, in which R is a linear or branched alkylene group containing 1 to 10 carbon atoms, to carboxylates, and on the other hand, of mononitriles, preferably aliphatic sulphurized mononitriles.

The method of the invention is particularly appropriate for the enzymatic synthesis of ammonium adipate from adiponitrile and ammonium methionate from methioninate.

The production of adipate determines a field of application of the invention in the synthesis of polyamides (NYLON®), whereas the production of methioninate particularly belongs to the field of application of animal feed.

The Examples which follow afford an illustration of the characteristics and advantages of the present invention without however limiting its scope.

DESCRIPTION OF THE FIGURES

FIGS. 4A and 4B show the DNA sequence SEQ ID NO: 4: according to the invention with its deduced amino acid sequence.

FIG. 5 shows the restriction map of plasmid pXL2087.

FIG. 6 shows the restriction map of plasmid pXL2148.

DETAILED DESCRIPTION OF EMBODIMENTS

The abbreviations used in the remainder of the description have the following meanings:

| | |
|---|---|
| SSC: | buffer commonly used for hybridizations, containing sodium citrate and NaCl (20x SSC = 3M NaCl, 0.3M sodium citrate, pH 7) |
| SDS: | sodium dodecylsulfate |
| FPLC: | fast protein liquid chromatography |
| SDS-PAGE: | gel electrophoresis based on sodium dodecylsulfate/polyacrylamide |
| IPTG: | isopropyl β-D-thiogalactopyranoside |

EXAMPLES

Example 1

PURIFICATION OF THE NITRILASE OF *COMAMONAS TESTOSTERONI* SP.

1—PREPARATION OF THE CELLS:

A strain of *Comamonas testosteroni* sp. was cultivated in a shake flask, at 28° C., for 15 h 30 min, in medium A having the following composition:

| Medium A | |
|---|---|
| Glucose | 5 g/l |
| $(NH_4)_2SO_4$ | 1 g/l |
| $Na_2HPO_4$ | 5.24 g/l |
| $KHPO_4$ | 2.77 g/l |
| Yeast extract | 5 g/l |
| Casamino acids | 1 g/l |

This preculture was used to inoculate a 20 l fermenter containing 15 l of medium A. The pH, temperature, air flow rate and shaking speed were set to 6.6, 28° C., 300 l/h and 350 rpm respectively. After 24 h, 84 g of wet cells were harvested. This corresponds to a content by dry weight of cells of 0.9 g/l and to an optical density at 660 nm ($OD_{660nm}$) of 2.

Figure 1:
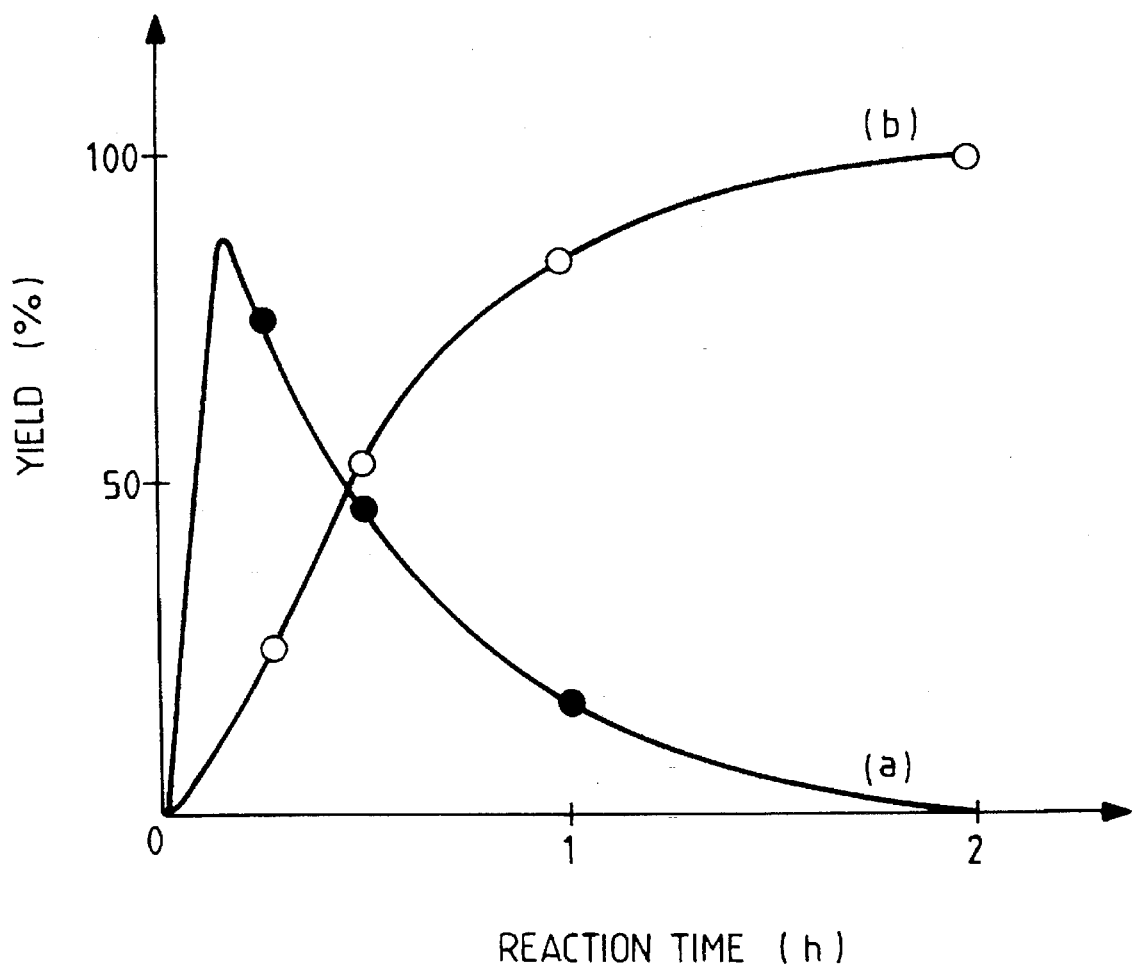
FIG. 1 shows the yield (%) of the hydrolysis of adiponitrile to cyanovalerate (curve a) and to ammonium adipate (curve b) as a function of the reaction time in hours for the strain Comamonas testosteroni sp.

2—DETERMINATION OF THE ENZYMATIC ACTIVITY ON ADIPONITRILE:

A cellular residue containing 13.1 mg of dry weight of cells was suspended in 2 ml of a 52.3 mM solution of adiponitrile in 50 mM potassium phosphate buffer, pH 7. The reaction was carried out at 25° C., with shaking, and the kinetics were followed by sampling. 5-Cyanovaleramide, adipamide, 5-cyanovalerate, adipamate and adipate were determined on each sample by high performance liquid chromatography (HPLC). The results are collated in FIG. 1, which shows the curves of the yield (on the ordinate) of cyanovalerate (curve a) and ammonium adipate (curve b). The respective rates of formation of cyanovalerate and adipate were greater than 0.45 and equal to 0.15 U/mg of dry weight of cells (1 U is equal to 1 μmol of product formed per minute).

3—PURIFICATION:

All the purification steps were carried out in 50 mM Tris/HCl buffer, pH 7.5, 1 mM dithioerythritol (DTE), unless indicated otherwise. At each step, the nitrilase activity of the fractions was determined at pH 7 and at 25° C. in 10 mM phosphate buffer in the presence of 10 mM adiponitrile. The protein concentration of the pools was determined by the Coomassie blue method (PIERCE Protein assay kit). The proteins were analyzed by SDS-PAGE (Phastsystem, PHARMACIA). The procedures of each step are discussed below.

Step 1: Crude extract 57 g of wet cells were taken up in 85 ml of buffer and treated with ultrasound for 30 min (VIBRACELL sonicator from Bioblock: probe 13 mm; power 7; 40% of the cycle active). The $OD_{660nm}$ thus dropped from 97 to 60. After centrifugation at a maximum of 48,000 g for 60 min, the supernatant was recovered.

This supernatant was brought to 15% saturation by the gradual addition of ammonium sulfate. After 1 h, the suspension was centrifuged for 30 min at a maximum of 30,000 g. The supernatant was brought to 50% saturation. After 1 h, the suspension was centrifuged under the same conditions and the precipitate was recovered and then dialyzed against the buffer for two days.

Step 2: Ion exchange column (Q Sepharose Fast Flow)

The dialyzed fraction was loaded at a rate of 125 ml/h on to a column (26×380 mm) of "Q Sepharose Fast Flow" equilibrated with the buffer at a rate of 250 ml/h. The column was percolated at a rate of 250 ml/h by the following solutions in succession:

166 ml of buffer 180 ml of a gradient of 0 to 0.2M KCl in the buffer 180 ml of buffer to which 0.2M KCl had been added 270 ml of a gradient of 0.2 to 0.4M KCl in the buffer 180 ml of buffer to which 0.4M KCl had been added 200 ml of buffer to which 1M KCl had been added The fraction having the nitrilase activity was eluted in a volume of 129 ml during the 0.2M KCl stage.

The following steps are carried out on the FPLC system (Pharmacia).

Step 3: Gel filtration (FPLC Superdex 200)

The previously obtained fraction having the nitrilase activity (129 ml) was concentrated to 12 ml by precipitation of the proteins with ammonium sulfate at 80% saturation, followed by dialysis against the buffer. The fraction concentrated in this way (12 ml) was loaded in 2 batches on to the column of gel (16×600 mm) equilibrated with the buffer to which 0.1M KCl had been added, at a rate of 0.8 ml/min. The fractions having the nitrilase activity were eluted with the above buffer at a rate of 1 ml/min and in a total volume of 36 ml. These fractions correspond to a molecular weight of 280 kDa.

Step 4: Column of hydroxyapatite (BIO-RAD HPHT; 7.8×100 mm)

The fractions obtained above were concentrated to 8 ml by ultrafiltration (DIAFLO PM39 membrane, AMICON). The concentrated solution was injected on to the column of hydroxyapatite equilibrated with the buffer to which 10 μM CaCl$_2$ had been added. The column was percolated at a rate of 0.5 ml/min with the following in succession:

5 ml of equilibration buffer 15 ml of a gradient of 0 to 350 mM potassium phosphate in the equilibration buffer 10 ml of the equilibration buffer to which 350 mM potassium phosphate had been added The fractions having the nitrilase activity were eluted between 62 and 135 mM potassium phosphate in a volume of 3 ml.

Step 5: Hydrophobic interaction column (FPLC-Phenyl Superose HR 5/5)

The active fractions obtained above, brought to 15% saturation with ammonium sulfate, were loaded at a rate of 0.5 ml/min on to the column equilibrated with buffer containing ammonium sulfate at 15% saturation. The column was percolated with:

6 ml of equilibration buffer 12 ml of a decreasing ammonium sulfate gradient of 15% to 0% ammonium sulfate saturation in the buffer 23 ml of buffer Some of the fractions having the nitrilase activity were eluted during the washing of the column with the equilibration buffer. These active fractions were reinjected under the same conditions. This operation was performed twice. The active fractions eluted after the gradient were pooled (volume 51 ml).

Step 6: Gel filtration (FPLC-Superdex 200)

The 51 ml were concentrated to 3 ml by ultra-filtration on a membrane (DIAFLO PM30, AMICON). These 3 ml were loaded on to the column (16×600 mm) equilibrated with the buffer to which 0.1M KCl had been added. The 9 ml containing the activity were eluted at a position corresponding to a molecular weight of 280 kDa. This solution was brought to 36% with glycerol and then frozen for 15 days.

Step 7: Ion exchange column (FPLC Mono Q HR 5/5)

The protein solution was thawed and loaded on to the column equilibrated with the buffer containing 0.1M KCl, at a rate of 0.5 ml/min. The column was percolated with the following in succession:

15 ml at 0.5 ml/min of buffer to which 0.1M KCl had been added 4.5 ml at 1 ml/min of buffer to which 0.1M KCl had been added 15 ml at 1 ml/min of a gradient of 0.1 to 0.4M KCl in the buffer 10 ml of buffer to which 0.4M KCl had been added The active fractions were eluted between 0.15 and 0.3M KCl. These fractions are homogeneous. SDS-PAGE analysis reveals two bands very close to 38 and 39 kDa. The fractions thus obtained will hereafter be called "purified nitrilase".

The data from each of the above purification steps are collated in Table 1 below:

TABLE 1

PURIFICATION OF THE NITRILASE OF *Comamonas testosteroni* sp.

| PURIFICATION STEP | Vol. ml | Proteine mg | ACTIVITY | | YIELD | | PF |
|---|---|---|---|---|---|---|---|
| | | | Total U | Specific U/mg | Protein % | Activity % | |
| 0-Crude Extract | 61 | 920 | 62,000 | 68 | 100 | 100 | 1 |
| 1-Q Sepharose FF | 130 | 245 | 47,000 | 190 | 27 | 76 | 2.8 |
| 3-Gel Filtration | 36 | 27 | 56,000 | 2,100 | 2.9 | 90 | 30 |
| 4-Hydroxyapatite Column | 3 | 12 | 49,000 | 4,100 | 1.3 | 79 | 60 |
| 5-Phenyl Superose | 51 | 11 | 11,000 | 1,000 | 1.1 | 18 | 15 |
| 6-Gel Filtration | 9 | 2.7 | 6,300 | 2,300 | 0.3 | 10 | 34 |
| 7-Mono Q HR 5/5 | 2.9 | 1 | 1,200 | 1,200 | 0.01 | 2 | 18 |

ABBREVIATIONS: PF = purification factor; U = 1 μmol/h

4—DETERMINATION OF THE N-TERMINAL SEQUENCE OF THE NITRILASE:

Taking the purified protein, the N-terminal sequence of 27 amino acids was determined by Edman automatic sequential degradation using an "Applied Biosystems Model 470 A" apparatus. This sequence, designated by SEQ ID NO: 1: in the enclosed sequence listing, is as follows:

Met Lys Asn Tyr Pro Thr Val Lys Val Ala Ala Val Gln Ala Ala Val Phe
             5                      10                   15

Met Asn Leu Glu Ala Thr Val Asp Lys Thr
            20               25

A search of sequence libraries made it possible to find a 53% identity with the nitrilase of *Klebsiella pneumoniae* active on bromoxynil, which forms the subject of European patent application no. 373 173.

5—ACTIVITY OF THE PURIFIED NITRILASE:

a)—Influence of the pH on the activity of the nitrilase:

The purified nitrilase was tested at different pH values on two substrates, adiponitrile and 5-cyanovalerate, under the conditions indicated in Table 2 below.

TABLE 2

ACTIVITY OF THE PURIFIED NITRILASE ON ADIPONITRILE AND CYANOVALERATE AS A FUNCTION OF THE pH

| SUBSTRATE | BUFFER Nature | pH | SPECIFIC ACTIVITY U/mg of protein |
|---|---|---|---|
| Adiponitrile | Acetate | 3.0 | 2,300 |
| | Acetate | 4.0 | 2,900 |
| | Acetate | 4.5 | 2,800 |
| | Acetate | 5.0 | 2,700 |
| | Phosphate | 6.0 | 2,900 |
| | Phosphate | 7.0 | 2,700 |
| | Phosphate | 8.0 | 2,800 |
| 5-Cyanovalerate | Acetate | 4.0 | 450 |
| | Acetate | 5.5 | 180 |
| | Phosphate | 7.0 | 30 |
| | Phosphate | 8.0 | 6 |

COMMON CONDITIONS: [substrate]=10 mM; buffer 10 mM; T 25° C.; [nitrilase]=12 µg/ml for cyanovalerate and 3 µg/ml for adiponitrile (fraction, step 6); U (adiponitrile)= µmol of cyanovalerate formed/h, U (cyanovalerate)=µmol of adipate formed/h.

b)—Activity range of the purified nitrilase:

The activities of the purified nitrilase were measured on adiponitrile, 5-cyanovaleramide, 5-cyanovaleric acid, benzonitrile, propionitrile and acrylonitrile. The results are given in Table 3.

TABLE 3

RELATIVE ACTIVITY OF THE PURIFIED NITRILASE ON VARIOUS NITRILES

| SUBSTRATE | RELATIVE ACTIVITY (%) |
|---|---|
| Adiponitrile | 100 |
| 5-Cyanovaleramide | 28 |
| 5-Cyanovaleric acid | 22 |
| Acrylonitrile | 23 |
| Propionitrile | 6 |
| Benzonitrile | 4 |

COMMON CONDITIONS: acetate buffer=10 mM, pH 4; substrate=10 mM; volume=3 ml; T=25° C.; reaction time=1 or 3 h; proteins: from 5 to 30 µg/ml.

Example 2

CLONING OF THE NITRILASE OF *Comamonas testosteroni* sp.

A nucleotide probe was synthesized from the NH$_2$-terminal sequence presented in Example 1; the high percentage of GC in the strains of Comamonas described in the literature (Tamaoka et al, Int. J. Syst. Bacteriol., 1987, 37, 52–59) dictated a choice for the third position of the codon in the case of lysines and in the case of valine. The probe is a 26 mer of degeneracy 128 (in the sequence of nucleotidic bases N replaces A, C, G or T):

| M K N Y | P T V | K V | Amino acids |
|---|---|---|---|
| 5' ATGAAGAATT | ATCCNACNGT | CAAGGT 3' | Nucleotidic Bases |
| C C | | G | (SEQ ID NO: 3:) Variants |

The MKNYPTVKV amino acid sequence given above corresponds to the SEQ ID NO: 2: in the enclosed sequence listing. The strategy followed consisted first of all in veri- fying the specificity of this nucleotide probe and determining the nature of the genomic DNA fragments to be cloned. Briefly, the genomic DNA of *Comamonas testosteroni* sp. was digested with several restriction enzymes (SstI, SphI, BamHI, PaI etc.) corresponding to sites usable for cloning.

After electrophoresis on agarose gel and transfer to a nylon membrane, the various digestions were hybridized with the probe. The probe is found to have a sufficient specificity under the hybridization conditions used (hybridization buffer=5×SSC, 5×Denhardt, 0.1% SDS, 50 mM Na$_3$PO$_4$, pH 6.5, 250 µg/ml of ssDNA; hybridization temperature 50° C.; washing conditions: 1 h, 6×SSC, room temperature, and 5 min, 2×SSC, 0.1% SDS, 50° C.).

Figure 2A:
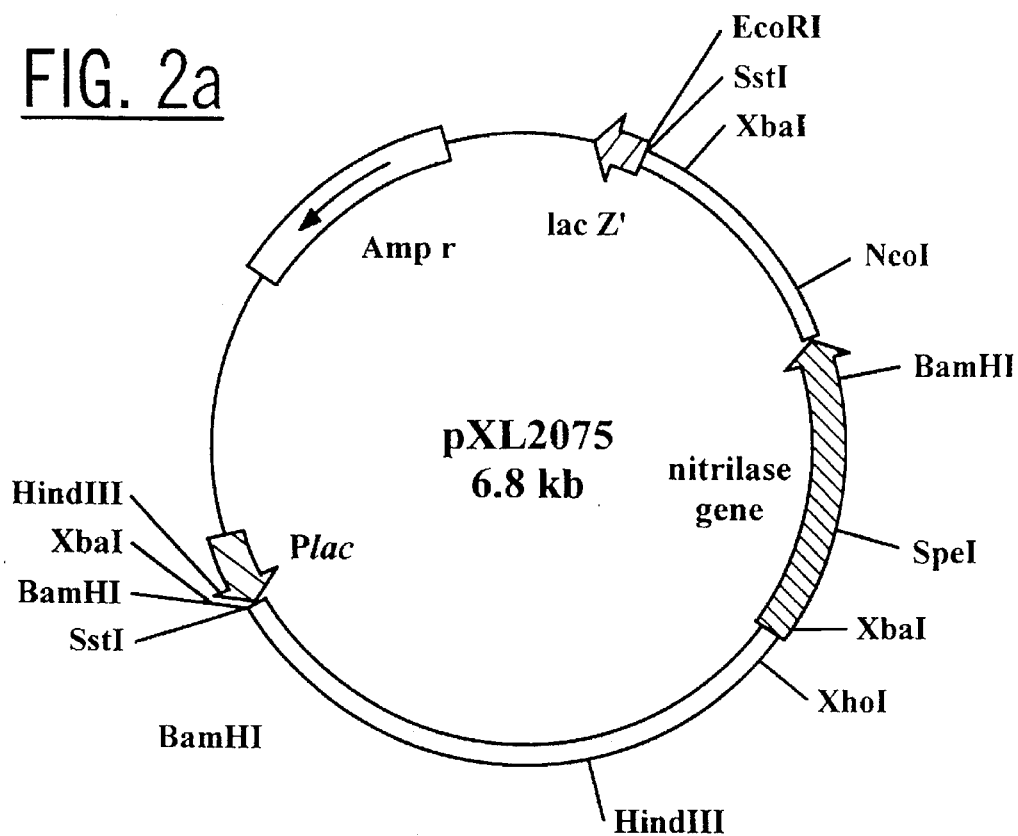
FIG. 2a and 2b show the restriction maps of plasmids pXL2075 and pXL2076.
Figure 2B:
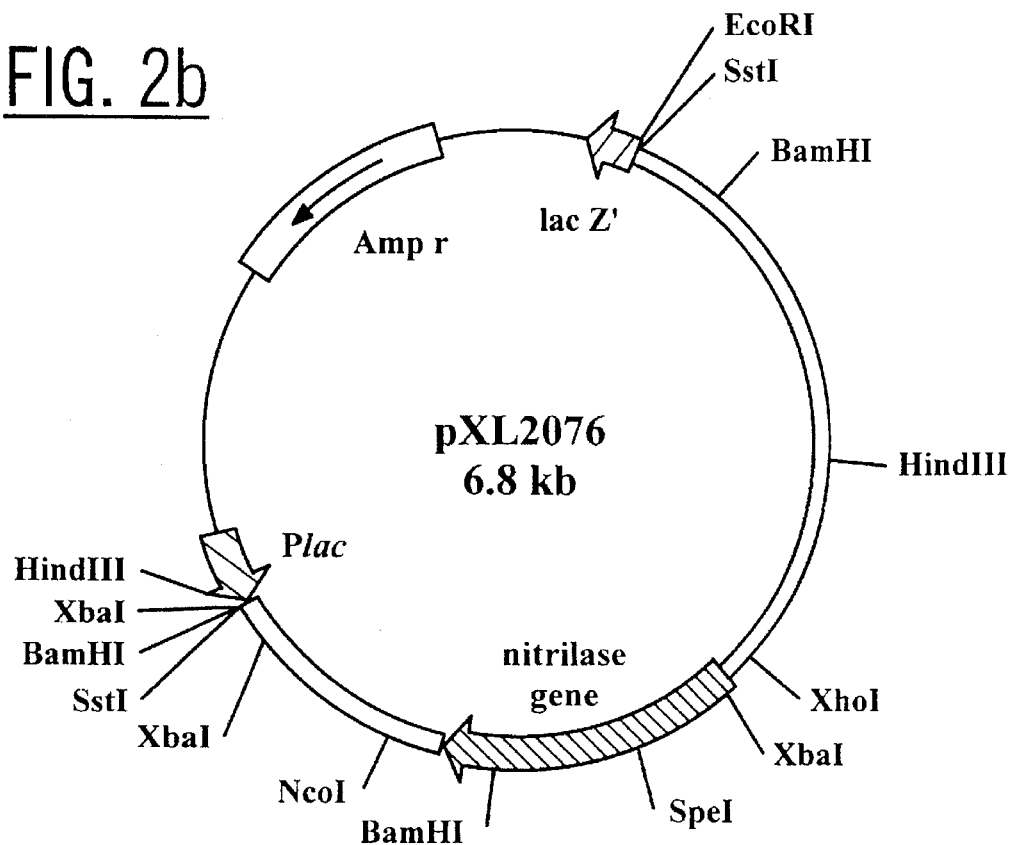

Under these conditions, the probe made it possible to obtain important signals without ambiguity, in particular in the case of digestions with SstI, SphI, BamHI and PstI. The hybridization blots show in particular the existence of a single SstI-SstI fragment of about 4 kb. To clone this fragment, the fragments of 3.5 to 4.5 kb from an SstI digestion of the genomic DNA were purified by preparative electrophoresis on agarose and electroelution and then ligated to plasmid pUC19 (YANISCH et al., Gene, 33 (1985) 103), itself digested with SstI. After transformation in the strain DH5α (Clontech Laboratory, Palo Alto, Calif.), 600 white clones on LB amp X-gal (SAMBROOK et al., Molecular Cloning, A Laboratory Manual, 2nd edition, Cold Spring Harbor Laboratory Press, Cold Spring Harbor Laboratory, N.Y., 1989) were subcultured individually, transferred to a nylon membrane and then analyzed by hybridization with the probe used to hybridize the Southern blot, under the same conditions of stringency. Six clones were thus identified as hybridizing very strongly with the probe. Two clones which had inserted the same fragment of about 4.1 kb in both orientations (pXL2075 [FIG. 2a] and pXL2076 [FIG. 2b]) were analyzed in greater detail (restriction mapping, partial sequencing using the probe as primer, and Southern blot). It was thus possible to show that the 5' part of the gene which hybridizes with the probe is located on an XhoI-XbaI fragment of about 150 bp orientated in the XhoI to XbaI direction. FIG. 2a and 2b show the restriction maps of these plasmids.

Example 3

SEQUENCE OF A FRAGMENT OF 1194 bp CONTAINING THE DNA CODING FOR THE POLYPEPTIDE HAVING THE NITRILASE ACTIVITY

Figure 3:
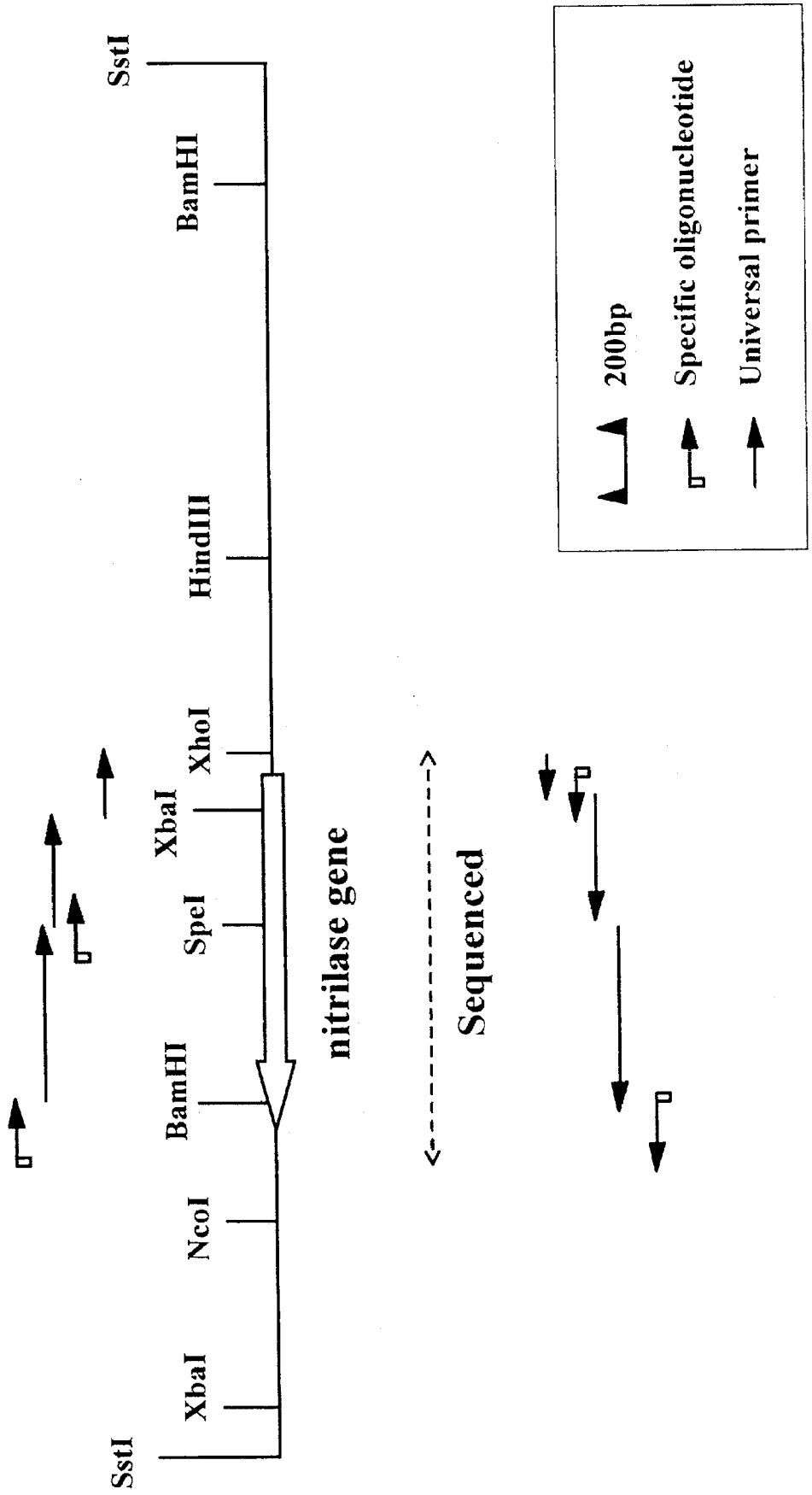
FIG. 3 shows the restriction map of the SstI-SstI fragment of 4.1 kb containing the DNA sequence (called "nitrilase gene" in the Figure) coding for the polypeptide having the nitrilase activity according to the invention, said fragment being present in plasmids pXL2075 and pXL2076. The strategy for producing the XbaI-SstI fragment containing the DNA sequence according to the invention is also shown in this Figure.

The location, on the cloned insert, of the fragment of 1194 bp containing the sequenced nitrilase gene is indicated in FIG. 3. The strategy for the sequencing of this fragment, performed by conventional methods known to those skilled in the art, is also indicated in FIG. 3. The various sequences were all obtained by the chain termination method (sequenase kit in the presence of 7-deaza-dGTP; ($^{35}$S)dATP either on single-stranded matrices of recombinant M13 (mp 18 or 19, see YANISCH et al., op. cit.) carrying subfragments, or directly on plasmid pXL2075). Several specific primers were also synthesized for this purpose.

The DNA sequence SEQ ID NO: 4: according to the invention is shown in FIG. 4A and 4B. The average G+C content of the sequence obtained is 45.7%, which is lower than the G+C content of 61.5% described for other strains of Comamonas (Tamaoka et al., op. cit.). An analysis of the sequence obtained made it possible to characterize an open reading frame of 1064 bp, hereafter called the nit gene, coding for a polypeptide of 354 residues corresponding to a molecular weight of 38,725 Da. The amino acid sequence of this polypeptide is indicated in SEQ ID NO :5: and in FIG. 4A and 4B. This polypeptide comprises the NH₂-terminal sequence used to synthesize the probe, as well as three internal sequences determined on tryptic fragments of the purified nitrilase (these internal sequences are underlined in FIG. 4A and 4B).

This open reading frame thus represents the DNA sequence according to the invention.

Example 4

HOMOLOGY WITH OTHER PROTEINS, IDENTIFICATION OF HOMOLOGOUS SEQUENCE.

The DNA sequence according to the invention was compared with all the sequences in the NBRF protein library; only one significant homology was found with the nitrilase of *Klebsiella ozaenae* specific for the herbicide Bromoxynil (Stalker et al., J. Biol. Chem., 1988, 263, 6310–6314). The two nitrilases exhibit a strict homology of 34.9% distributed over 320 amino acids. Furthermore, this protein exhibits a strict homology of 34.4%, distributed over 312 amino acids, with the nitrilase of Arabidopsis specific for indole-3-acetonitrile [Bartling et al., Eur. J. Biochem., 205, 417–424, 1992].

Example 5

EXPRESSION OF THE NITRILASE IN *E. coli*

To confirm the identification of the coding frame with the purified nitrilase, the nit gene, preceded by its own ribosome binding site, was placed under the control of the lactose operon promoter of *E. coli* in accordance with the procedure described below: Plasmid pXL2087, described in FIG. 5, was obtained by insertion of the XhoI-NcoI fragment derived from plasmid pXL2075 between the corresponding sites of vector pMTL25 (Chambers et al., Gene, 1988, 6–8, 139–149). This plasmid therefore contains the lactose operon promoter Plac, followed by the ribosome binding site and the structural nitrilase gene, as well as a gene conferring ampicillin resistance. The expression of the nitrilase was visualized in the strain *E. coli* TG1 containing plasmid pXL2087. For this purpose, the strain TG1/pXL2087 and the control strain TG1/pUC19 were cultivated for 16 h at 37° C. in LB medium (Miller, J. H., 1972, Experiments in Molecular Genetics—Cold Spring Harbor Laboratory, Cold Spring Harbor, N.Y.) containing 100 µg/ml of ampicillin, and then diluted 100-fold in the same medium and at the same temperature. When the cultures had reached an OD₆₁₀ of between 0.5 and 1, IPTG was added at a final concentration of 1 mM. After 2 h of culture, the bacteria were collected.

Figure 7:
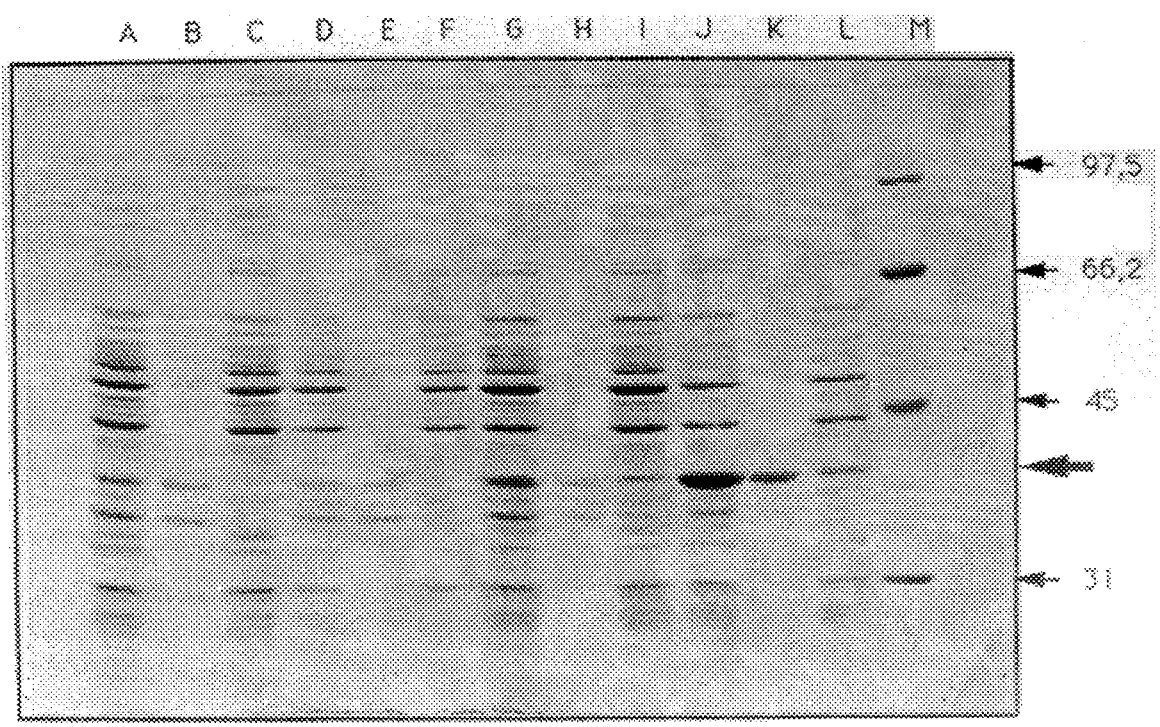
FIG. 7 shows the SDS-PAGE, 10% SDS, indicating the expression of the DNA sequence according to the invention in the strain *E. coli* TG1/pXL2027. Each lane corresponds to an amount of protein equivalent to 60 μl of culture at an optical density of 3 at 610 nm.

After sonication of the cells, the expression of the nitrilase was measured by SDS-PAGE in the crude fraction or, after centrifugation, in the residue and the supernatant. The results are presented in FIG. 7 and show a high level of expression of the nitrilase in the extracts of cells cultivated in the presence of IPTG; however, this protein is essentially in insoluble form. In FIG. 7, M represents the molecular weight marker; the molecular weights are indicated in kDa. Also, the lanes have the following meanings:

|  | TG1 + pUC19 | TG1 + pUC19 + IPTG | TG1 + pXL2087 | TG1 + pXL2087 + IPTG |
| --- | --- | --- | --- | --- |
| Crude Fractions | A | D | G | J |
| Residues | B | E | H | K |
| Supernatants | C | F | I | L |

Starting from plasmid pXL2087, plasmid pXL2148 was prepared by insertion of the XhoI-EcoRI fragment of plasmid pXL2087, carrying the gene coding for the nitrilase, between the SalI and EcoRI sites of pBR322 [SUTCLIFFE, Nucleic Acid Res., 5 (1978) 2721–2730].

This plasmid pXL2148, whose restriction map is shown in FIG. 6, was also used to transform the strain *E. coli* TG1 by the calcium chloride method. The microorganisms were selected on ampicillin. The strain *E. coli* TG1 (pXL2048) (G4207) transformed in this way was deposited in the Collection Nationale de Cultures de Micro-organismes in Paris (Institut Pasteur, 25 rue du Docteur Roux) under no. 1-1242 on 21st Jul. 1992. Other expression systems were used to produce the nitrilase in a recombinant microorganism.

First of all, the nit gene was expressed in *E. coli* behind the tryptophan operon promoter of *E. coli* under the dependence of the RBS of the phage λ CII gene. To do this, an NdeI restriction site was created on the initiation codon of nit, and the NdeI/AhaII fragment of 117 bp, containing the 5' part of the nit gene, was amplified by the PCR technique starting from pXL2087. An NdeI/XbaI fragment of 61 bp, obtained after digestion of the first fragment, was ligated to the EcoRI/NdeI fragment containing the tryptophan operon promoter of *E. coli* and the ribosome binding site of the bacteriophage λ CII gene (Ptrp-RBSCII) between the EcoRI and XbaI sites of pUC19 (Yanisch et al., Gene, 33 (1985) 103) to give plasmid pXL2149. The EcoRI/XbaI fragment of pXL2149, containing the 5' part of nit behind Ptrp-RBSCII, was ligated to the XbaI/SalI fragment of pXL2087 containing the 3' part of the nit gene between the EcoRI and SalI sites of pXL642 (Mayaux, unpublished results): pXL642 is a derivative of pXL534 (Latta et al., 1990, DNA Cell Biol., 9, 129) in which the superexpressed gene codes for a tissue inhibitor of metalloproteases and in which the HindIII site downstream from the superexpressed gene has been replaced by the EcoRI/HindIII multisite of M13mp18.

Figure 8:
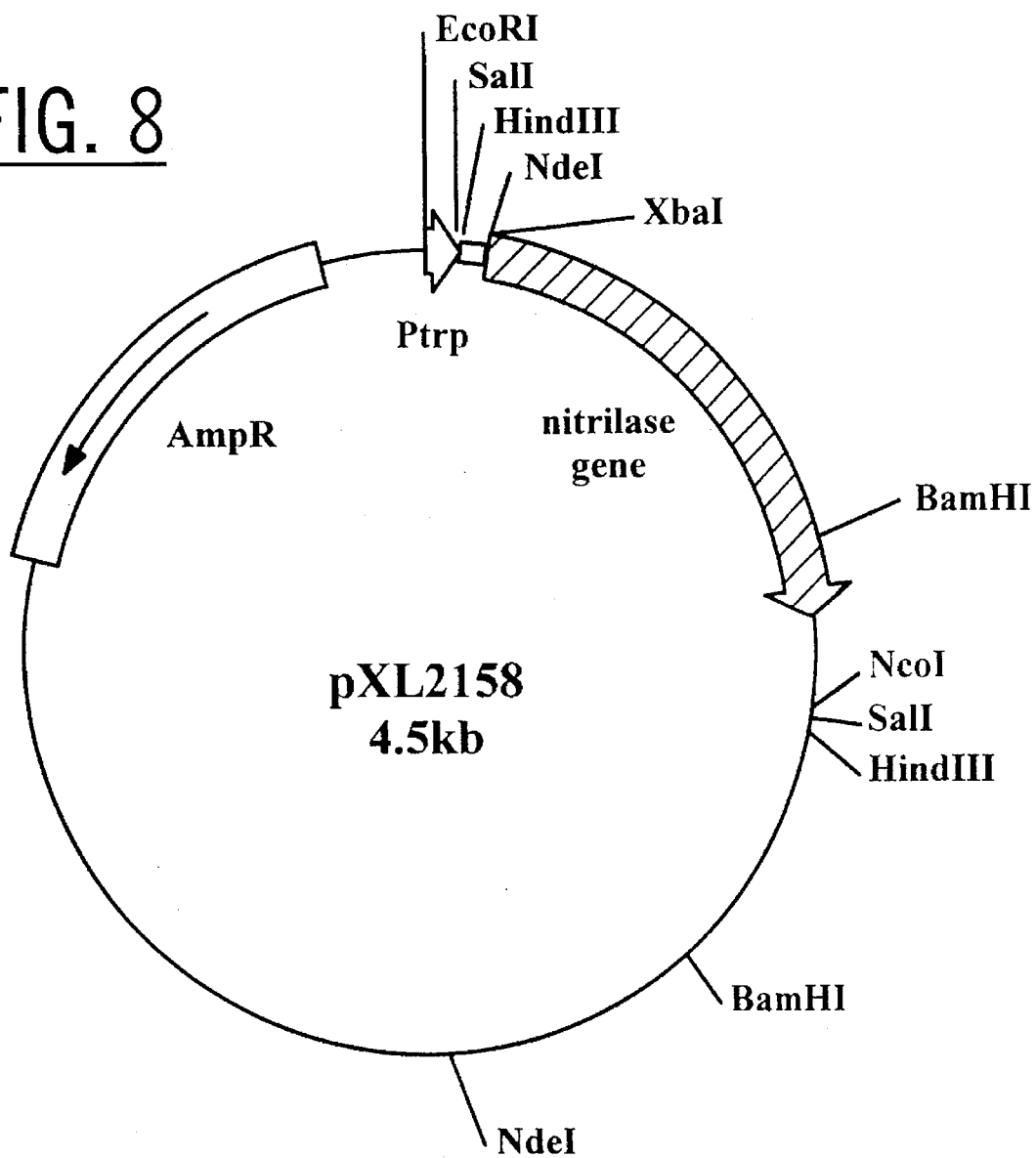
FIG. 8 shows the restriction map of plasmid pXL2158.

The final plasmid pXL2158 is therefore a derivative of pBR322 (Sutcliffe, Nucleic Acid Res., 5 (1978) 2721) containing a gene conferring ampicillin resistance and the nit gene under the control of Ptrp-RBSCII. The restriction map of this plasmid pXL2158 is shown in FIG. 8.

Plasmid pXL2158 was used to transform the strain *E. coli* TG1. The strain TG1/pXL2158 and the control strain TG1 containing vector pMTL22 were cultivated for 16 h at 30° C. in M9 glucose medium (Miller, J. H., 1972, Experiments in Molecular Genetics, Cold Spring Harbor Laboratory, Cold Spring Harbor, N.Y.) containing 100 µg/ml of ampicillin and 100 µg/ml of tryptophan. These cultures were diluted 100-fold in the same medium, but without tryptophan, and cultivated for 6 hours at the same temperature.

After sonication of the cells, the expression of the nitrilase of *Comamonas testosteroni* NI 1 was measured in 12.5%

Figure 9:
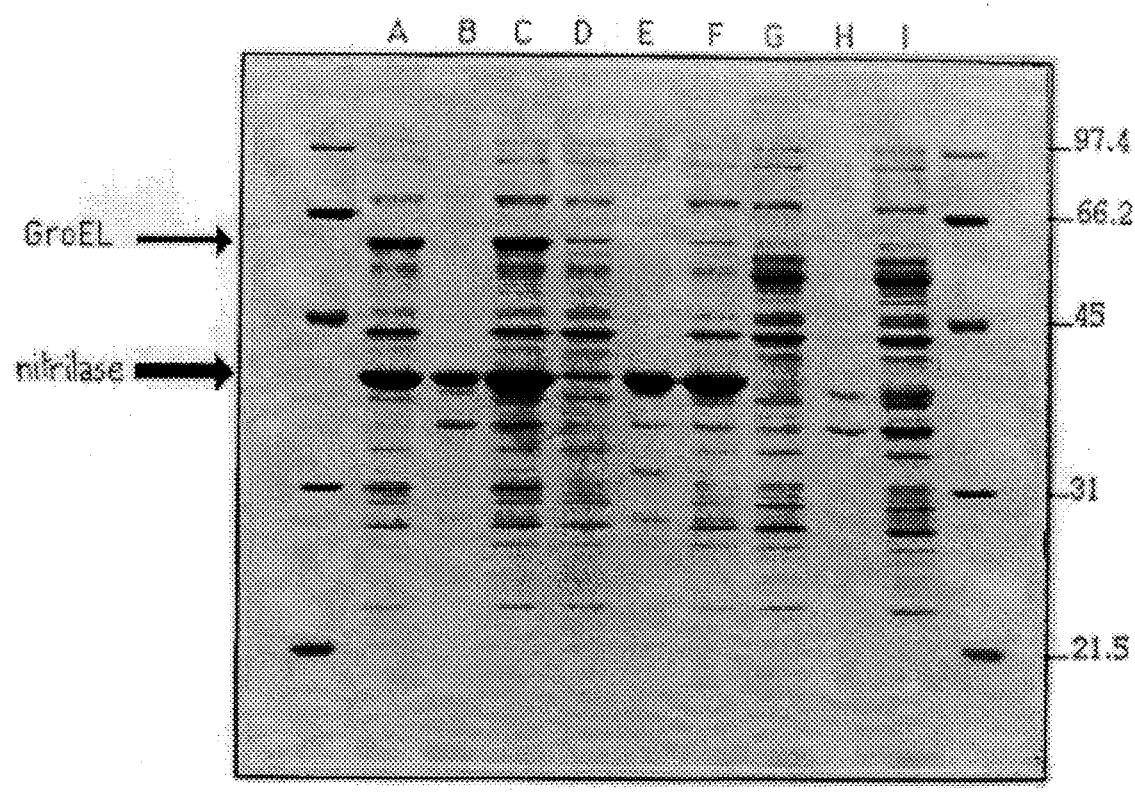
FIG. 9 shows the SDS-PAGE, 12.5% SDS, indicating the expression of the DNA sequence according to the invention in the strains TG1/pXL2158 and TG1/pXL2158+pXL2035 (GroE).

SDS-PAGE in the crude fraction or, after centrifugation, in the residue and in the supernatant. The results are shown in FIG. 9.

|  | TG1/pXL2158 + pXL2035 | TG1/pXL2158 | TG1 + pMTL22 |
|---|---|---|---|
| Supernatant | A | D | G |
| Residue | B | E | H |
| Total Extract | C | F | I |

This gel shows that pXL2158 induces a strong expression of the nitrilase, predominantly in insoluble form.

The efficacy of the GroE chaperone was then tested (Hemmingsen et al., 1988, Nature, 333, 330) in order to assist the correct folding of the nitrilase. For this purpose, plasmid pXL2035 was constructed in the following manner. The EcoRl/HindIII fragment of 2.2 kb, containing the groES and qroEL genes coding for the two subunits of GroE, was extracted from plasmid pOF39 (Fayet et al., 1986, Mol. Gen. Genet., 202, 435) and introduced between the EcoRI and HindIII sites of vector pDSK519 (Keen et al., 1988, Gene, 70, 191).

Plasmid pXL2035 was introduced into the strain TG1 containing pXL2158. The resulting strain was cultivated under the same conditions as before, in the presence of 50 mg/l of kanamycin; the expression results are visualized in FIG. 9. It is found that the superexpression of GroE (only the GroEL subunit is visible on the gel) solubilizes the bulk of the nitrilase expressed from pXL2158.

The same expression system was used to produce the nitrilase in Pseudomonas putida. Thus, starting from pXL2158, the NdeI/NcoI fragment of 1256 bp and the NcoI/BamHI fragment of 535 bp were introduced between the NdeI and BamHI sites of pXL1841. pXL1841 (Blanche et al., 1991, J. Bacteriol., 173, 4637) is a derivative of pKT230 (Bagdasarian et al., 1981, Gene, 15, 237) expressing a Methanobacterium ivanovii gene behind Ptrp-RBSCll.

Figure 10:
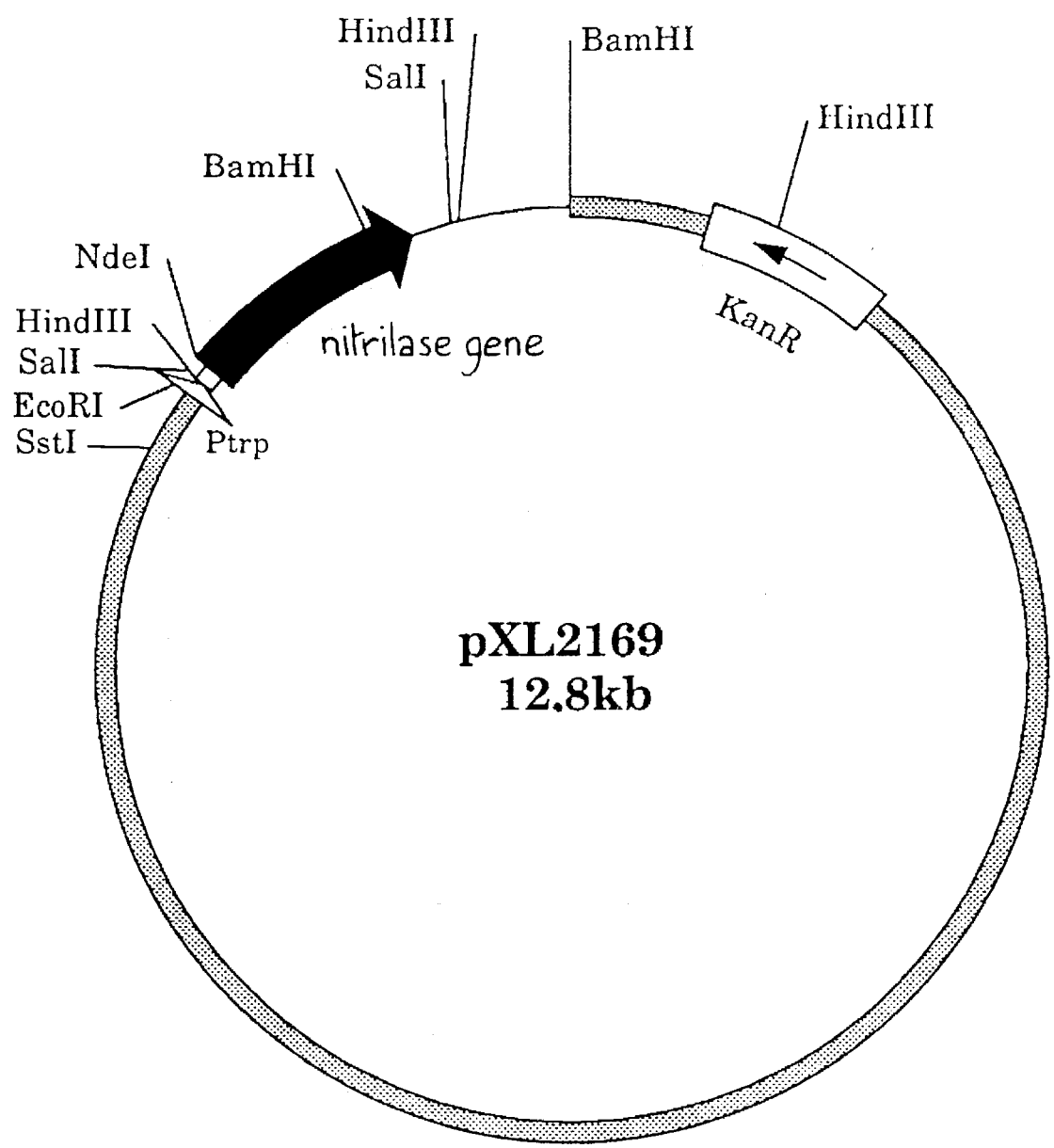
FIG. 10 shows the restriction map of plasmid pXL2169.

The final plasmid pXL2169 is therefore a derivative of pKT230 containing a gene conferring kanamycin resistance and the nit gene under the control of Ptrp-RBSCll (see FIG. 10). This plasmid was introduced into the strain Pseudomonas putida G2081. G2081 is a derivative of Pseudomonas putida KT2440 (Bagdasarian and Timmis, 1981, in Hofschneid and Goebel, Topics in Microbiology and Immunology, 47, Springer Verlag, Berlin) rendered resistant to nalidixic acid and rifampicin. Vector pDSK519 (Keen et al., 1988, Gene, 70, 191) was used as the control plasmid. G2081 (pXL2169) and the strain G2081 (pDSK519) were cultivated overnight at 30° C. in LB medium containing 20 mg/l of kanamycin. These precultures were diluted 100-fold in the same medium. The cultures were then continued for 7 h 30 min at the same temperature.

Figure 11:
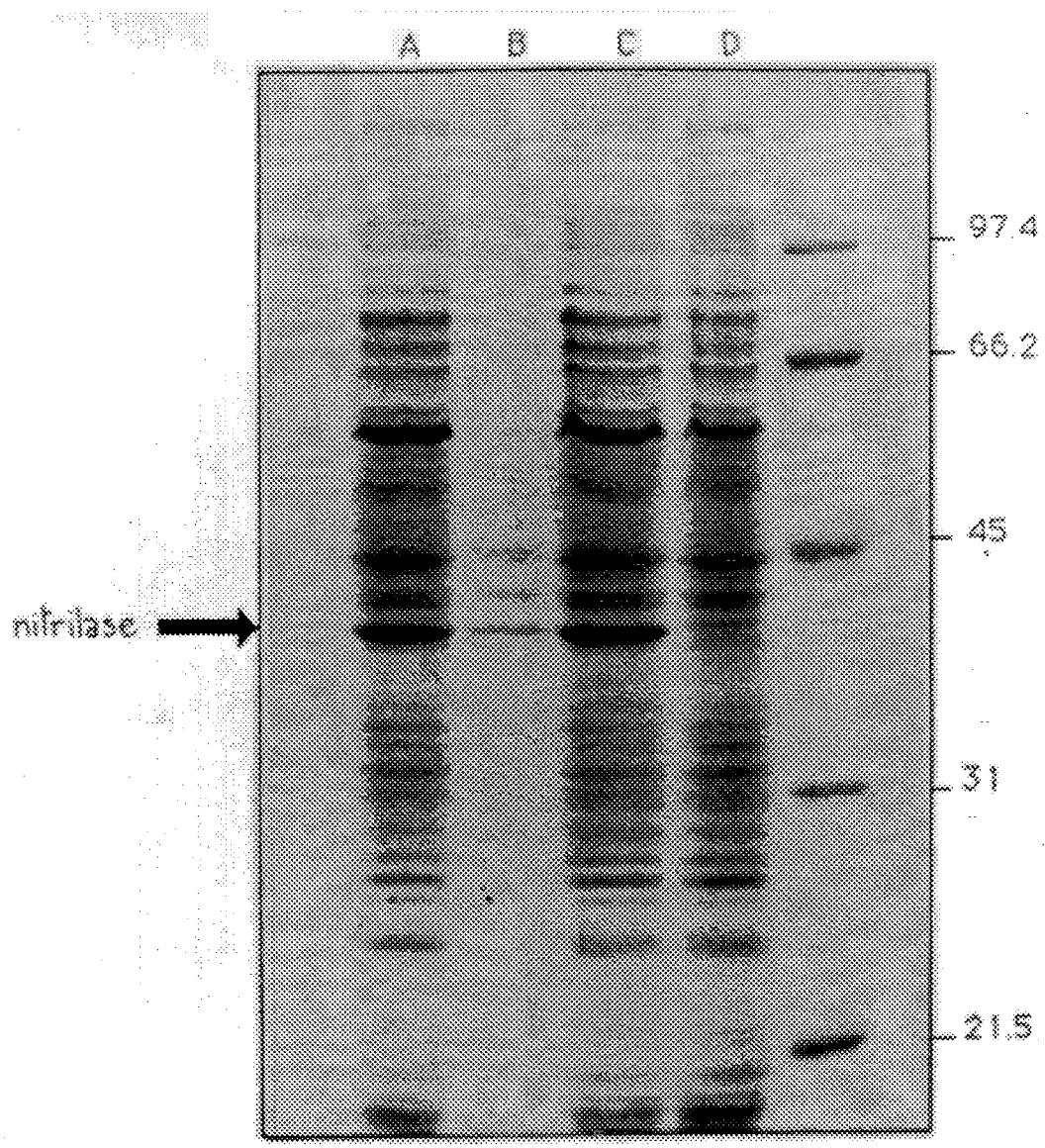
FIG. 11 shows the SDS-PAGE, 10% SDS, indicating the expression of the DNA sequence according to the invention in the strain *Pseudomonas putida* G2081-pXL2169.
Figure 12:
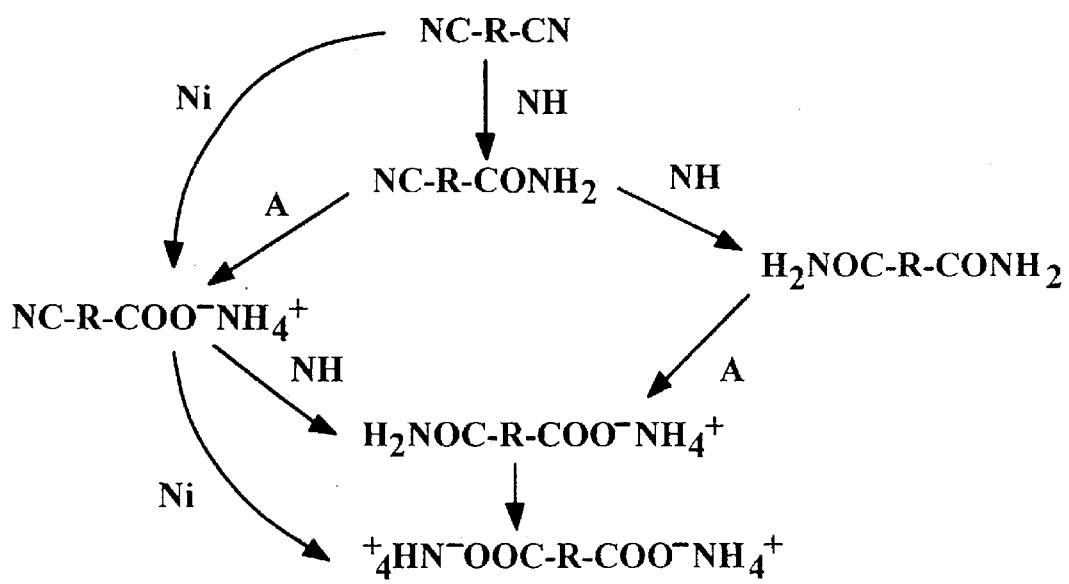
FIG. 12 shows the theoretical scheme for enzymatic hydrolysis of dinitriles, wherein NH=nitrile hydratase; Ni=nitrilase; A=amidase; and R=$(CH_2)_n$, n being an integer equal to 4 in the case of adiponitrile.

After sonication of the cells, the expression of the nitrilase of Comamonas testosteroni NI 1 was measured in 10% SDS-PAGE in the crude fraction or, after centrifugation, in the residue and in the supernatant. The results are presented in FIG. 11. Only the crude extract of the strain G2081 (pDSK519) was deposited (well D). For the strain G2081 (pXL2169), the total extract, the sonication residue and the sonication supernatant were deposited in wells C, B and A respectively. This experiment shows that the strain of Pseudomonas putida expresses large amounts of nitrilase in soluble form.

Example 6

ASSAY OF THE NITRILASE ACTIVITY OF RECOMBINANT STRAINS

The Examples which follow illustrate the nitrilase activity of the recombinant strains E. coli TG1 and Pseudomonas putida G2081.

The different plasmids integrated into these strains are as follows:

| PLASMIDS | CHARACTERISTICS |
|---|---|
| pXL2087 | Recombinant plasmid which carries the Comamonas NI 1 nitrilase gene under the control of the promoter $P_{lac}$. |
| pXL2158 | Recombinant plasmid which carries the Comamonas NI 1 nitrilase gene under the control of the tryptophan promoter. |
| pXL2035 | Recombinant plasmid which carries the genes coding for GroE and S. |
| pXL2169 | Broad host range plasmid with an insertion, carrying the Comamonas NI 1 nitrilase gene under the control of $P_{trp}$. |
| pDSK519 | Control plasmid (see page 24 line 18). |

The activities of these strains, induced or non-induced, are measured on adiponitrile and 5-cyanovalerate at different pH values and are compared with the negative control strains: E. coli TG1, E. coli TG1 (pXL2035) and Pseudomonas putida G2081.

6.1—PREPARATION OF THE CELLS:

The cultures are carried out under the conditions described in Table 4. During the exponential growth phase, one of the two cultures of the recombinant strain is induced with 1 mM IPTG; after 2 h at 37° C., this culture is treated.

TABLE 4

CULTURE OF THE STRAINS

| MICROORGANISMS | MEDIUM | $OD_{660\,nm}$ | DW (g/l) |
|---|---|---|---|
| 1-E. coli TG1 | a | 3.1 | 0.90 |
| 2-E. coli (pXL2087) | b | 3.2 | 0.90 |
| 3-E. coli (pXL2087) | c | 2.5 | 0.90 |
| 4-E. coli (pXL2035) | d | 2.1 | 0.90 |
| 5-E. coli (pXL2158) | b | 3.1 | 0.80 |
| 6-E. coli (pXL2035, 2158) | e | 4.2 | 1.30 |
| 7-P. putida (pXL1289) | d | 2.1 | 0.98 |
| 8-P. putida (pXL2169) | d | 2.3 | 0.98 |

ABBREVIATIONS: a = LB medium; b = LB medium + 100 µg/ml of Amp; c = medium b + addition of 1 mM IPTG to $OD_{660\,nm}$ = 1; d = LB medium + 50 mg/l of kanamycin; e = M9 medium + 100 mg/l of ampicillin + 50 mg/l of kanamycin; DW = dry weight..

COMMON CONDITIONS:

1 to 3: Inoculation in a ratio of 1/100 with a 16-hour-old preculture; culture time 5.75 h; T 37° C.

4 to 8: Inoculation in a ratio of 1/100 with a 17-hour-old preculture at 37° C. with the addition of tryptophan; culture time in 15 l fermenter: 23 h for E. coli and 7.5 h for P. putida; T 30° C.

6.2—SPECIFIC ACTIVITY MEASUREMENTS:

The conditions of the specific activity measurements and the results are collated in Table 5.

TABLE 5

DETERMINATION OF THE ACTIVITIES OF THE CONTROL STRAINS FOR THE RECOMBINANT STRAINS

| MICROORGANISM | | | | OPERATING CONDITIONS | | | | |
|---|---|---|---|---|---|---|---|---|
| | | | | [DW] | Volume | | Activity | |
| Nature | IPTG | State | Substrate | (g/l) | (ml) | pH | Ua | Ub |
| 1-E. coli TG1 | – | W | CVA | 15.5 | 1 | 5.2 | | 0 |
| | – | W | CVA | 15.5 | 1 | 7.0 | | 0 |
| | – | W | AdN | 15.5 | 1 | 5.2 | | 0 |
| | – | W | AdN | 15.5 | 1 | 7.0 | | 0 |
| 2-E. coli TG1 | + | W | CVA | 1.4 | 1 | 4.0 | | 28 |
| pXL2087 | + | W | CVA | 1.4 | 1 | 5.2 | | 27 |
| | + | W | CVA | 1.4 | 2 | 7.0 | | 8 |
| | + | S | CVA | 1.4 | 1 | 5.2 | | 25 |
| | + | S | CVA | 1.4 | 2 | 7.0 | | 8 |
| | + | W | AdN | 0.3 | 1 | 4.2 | 159 | |
| | + | W | AdN | 1.4 | 1 | 4.3 | | 38 |
| | + | W | AdN | 1.4 | 2 | 6.2 | | 18 |
| | + | W | AdN | 1.4 | 2 | 7.0 | | 11 |
| | + | S | AdN | 1.4 | 2 | 6.2 | | 17 |
| | + | S | AdN | 1.4 | 2 | 7.0 | | 10 |
| 3-E. coli TG1 | – | W | CVA | 1.2 | 2 | 4.0 | | 10 |
| pXL2087 | – | W | CVA | 1.2 | 2 | 5.2 | | 14 |
| | – | W | CVA | 1.2 | 2 | 7.0 | | 3.4 |
| | – | S | CVA | 1.0 | 1 | 5.2 | | 13 |
| | – | S | CVA | 1.0 | 1 | 7.0 | | 3.2 |
| | – | W | AdN | 0.3 | 1 | 4.2 | 75 | |
| | – | W | AdN | 1.2 | 2 | 4.3 | | 16 |
| | – | W | AdN | 1.2 | 2 | 6.2 | | 11 |
| | – | W | AdN | 1.2 | 2 | 7.0 | | 3.4 |
| | – | S | AdN | 1.0 | 1 | 6.2 | | 3 |
| | – | S | AdN | 1.0 | 1 | 7.0 | | 4 |
| 4-E. coli TG1 pXL2035 | – | W | AdN | 0.06 | 1 | 7.0 | 0 | 0 |
| 5-E. coli TG1 | – | W | AdN | 0.24 | 1 | 7.0 | 270 | |
| pXL2158 | | | CVA | 1.25 | 1 | 7.0 | | 8.3 |
| 6-E. coli TG1 | – | W | AdN | 0.06 | 1 | 7.0 | 1500 | |
| pXL2035,2158 | | | CVA | 0.2 | 1 | 7.0 | | 70 |
| 7-P. putida G2081 pDSK519 | – | W | AdN | 0.3 | 1 | 7.0 | 0 | |
| 8-P. putida G2081 pXL2169 | – | W | CVA | 0.25 | 1 | 7.0 | 130 | |

COMMON CONDITIONS: [substrate]=50 mM; T=25° C.; buffer 50 mM; kinetics over 90 min for 1 to 3 and over 120 min for 4 to 8.

ABBREVIATIONS: W=whole cells; S=sonicated cells; Ua=μmols of cyanovalerate produced/h; Ub=μmols of adipate produced/h; AdN=adiponitrile; CVA=5-cyanovalerate. DW=dry weight.

Example 7

SYNTHESIS OF AMMONIUM ADIPATE BY THE BATCH HYDROLYSIS OF ADIPONITRILE WITH E. coli (pXL2087) IN SUSPENSION 120 μl or 1068 μmol of adiponitrile were added at 25° C. and with magnetic stirring, at the reaction times 0, 1, 2, 3, 5, 6 and 7 h, to an initial volume of 5 ml of 50 mM phosphate buffer, pH 7, containing the strain E. coli (pXL2087) at an initial concentration of 21 g/l. The reaction was monitored analytically by taking 100 μl samples of the reaction volume every hour. The hydrolysis was found to proceed without a notable loss of kinetics.

The mean activities calculated over 30 min after addition of the adiponitrile are collated in Table 6 below.

TABLE 6

MEAN ACTIVITIES OF THE E. coli (pXL2087) CELLS DURING THE HYDROLYSIS OF ADIPONITRILE

| REACTION TIME (h) | SPECIFIC ACTIVITY μmol of adipate/h x mg of dry cells |
|---|---|
| 0.5 | 16 |
| 2.5 | 15 |
| 5.5 | 11 |
| 6.5 | 11 |
| 7.7 | 15 |

Example 8

SYNTHESIS OF AMMONIUM ADIPATE BY THE HYDROLYSIS OF ADIPONITRILE IN A FIXED BED REACTOR WITH E. coli (pXL2087) IMMOBILIZED ON RESIN The E. coli (pXL2087) cells were first fixed by the technique described in U.S. Pat. No. 4,732,851.

The resulting biocatalyst was then used in a fixed bed column for the hydrolysis of adiponitrile to ammonium adipate.

8.1—FIXING OF E. coli (pXL2087) TO RESIN:

The cells were fixed according to the following protocol:

1 g (wet weight) of E. coli (pXL2087) with a solids content of 22%, 1 g of POLYCUP polyazetidine, 1 g of DUOLITE A 171 resin.

The gram of cells was suspended in the polyazetidine solution. After homogenization, the resin was poured into the cell suspension. The whole was stirred with a spatula and then left to dry for 18 h, open to the air, under a hood. 4 ml or 1.3 g of biocatalyst were thus collected. The activities of the immobilized and free cells were determined at 25° C. and pH 7 on a 50 mM solution of adiponitrile. They are respectively 30 and 110 µmol of 2-cyanovalerate/h/mg of cells DW, from which a fixing yield of 26% is deduced.

8.2—HYDROLYSIS OF ADIPONITRILE IN A FIXED BED REACTOR:

The half-life is determined in a continuously fed fixed bed reactor under the conditions indicated below:

T 28° C.; catalyst 0.5 g or 2 ml or 85 mg of cells (dry weight); [adiponitrile] 50 mM; phosphate buffer 50 mM, pH 7; flow rate 3.7±0.1 ml/h; column: diameter 1 cm, height 3 cm.

The initial activity of the cells was 1.5 µmol of adipate/h/mg of cells (dry weight). 66% of the initial activity is preserved after 32 days or 770 h.

Example 9

SYNTHESIS OF AMMONIUM METHIONINATE BY HYDROLYSIS OF METHIONONITRILE, WITH RECOMBINANT STRAINS IN SUSPENSION

The recombinant strains used in this example are those from E. coli TG1, integrating the plasmids PXL2158 and PXL2035 described above and containing the nitrilase gene of Comamonas testosteroni.

Tests 9 to 13 show the nitrilase activity at 28° C., of these recombinant strains with respect to the methiononitrile, according to various operating conditions. The strain culture is performed as explained in example 6.1.The following Table 7 summarizes the conditions and the results of tests 9 to 13.

activity which is almost 10 times greater: about 80 µmol of MEtCN/hxmg of DW. Tests 11 to 13 show that the initial quantity of MetCN substrate has only a small influence on the activities obtained.

Example 10

SYNTHESIS OF AMMONIUM METHIONINATE BY HYDROLYSIS OF METHIONONITRILE, WITH E. coli PXL 2158 +2035 CELLS FIXED ON RESIN The E. coli PXL 2158+2035 free cells are fixed on resin according to the technique described in U.S. Pat. No. 4,732,851, so as to form a biocatalyst.

10.1—FIXING YIELD AND ACTIVITY OF THE BIOCATALYST:

The results of the initial activities of the biocatalyst and of the free cells are given in Table 8 below.

TABLE 8

SPECIFIC INITIAL ACTIVITIES OF HYDROLYSIS OF THE METHIONONITRILE OF THE FREE AND FIXED CELLS OF E. coli PXL2158 + 2035

| | | | Specific Initial Activity | |
| --- | --- | --- | --- | --- |
| Test No. | Dry biocatalyst g/l | Dry cells g/l | µmol/hxmg DB | µmol/hx mg DC |
| 14 | 10.3 | 1.4 | 3 | 22 |
| 15 | — | 1.3 | — | 63 |

CONDITIONS: volume=5 ml; potassium phosphate buffer=100 mM pH7, [MetCN]=50 mM; T 28° C.; kinetics over 3 h; DB=dry biocatalyst; DC=dry cells.

COMMENTS: the activity of the biocatalyst is 3 µmol/hxmg of dry biocatalyst at 28° C. and the fixing yield is 35%.

With the free or fixed cells, 5% to 6% of amides are produced at the end of the hydrolysis.

TABLE 7

| MICROORGANISM | | OPERATING CONDITIONS | | | | Initial specific activity µmol/h |
| --- | --- | --- | --- | --- | --- | --- |
| Nature | State | Substrate (mM) | [DW] (g/l) | Volume (ml) | pH | x mg of DW |
| 9-E. coli PXL2158 | W | MetCN (100) | 17.2 | 5 | 7 | 8 |
| 10-E. coli PXL2158 + 2035 | W | MetCN (50) | 1.4 | 5 | 7 | 77 |
| 11-E. coli PXL2158 + 2035 | W | MetCN (50) | 1.4 | 5 | 7 | 62 |
| 12-E. coli PXL2158 + 2035 | W | MetCN (100) | 1.4 | 5 | 7 | 73 |
| 13-E. coli PXL2158 + 2035 | W | MetCN (200) | 1.4 | 5 | 7 | 61 |

ABBREVIATIONS: W = whole cells; DW = dry weight of cells; MetCN = methiononitrile.

COMMENTS ON TABLE 7: Tests 9 and 10 show that the recombinant strain E. coli PXL2158 possesses a good nitrilase activity but that it is recombinant strain E. coli combining PXL2158 and PXL2035, which is the most interesting strain as regards performances, thanks to an 10.2—INFLUENCE OF THE INITIAL METHIONONITRILE CONCENTRATION:

Two methiononitrile batches were tested: purified methiononitrile in the form of a sulfate and free methiononitrile. The results are summarized in Table 9 below.

TABLE 9

INFLUENCE OF THE INITIAL METHIONONITRILE CONCENTRATION ON THE SPECIFIC INITIAL ACTIVITY OF E. coli PXL2158 + 2035

| TEST No. | [MetCN] sulfate mM | [MetCN] Free mM | Dry biocatalyst g/l | Specific initial activity μmol/hxmg DB | Specific initial activity μmol/hxmg DC | Amide formed* % |
|---|---|---|---|---|---|---|
| 16 | 50 | — | 10.3 | 3.0 | 22.0 | 5.9 |
| 17 | 100 | — | 10.0 | 3.4 | 25.1 | 6.0 |
| 18 | 200 | — | 10.5 | 4.2 | 30.5 | 8.3 |
| 19 | 300 | — | 10.2 | 4.2 | 30.5 | 10.6 |
| 20 | — | 105 | 9.9 | 2.7 | 20.0 | 9.6 |
| 21 | — | 210 | 10.0 | 2.9 | 20.8 | 12 |
| 22 | — | 315 | 9.7 | 2.4 | 17.7 | 16 |

CONDITIONS: volume=5 ml; potassium phosphate buffer=100 mM pH7; T 28° C.; kinetics over 3 h; *=percent with respect to the formed acid; DB=dry biocatalyst; DC=dry cells.

COMMENTS: the specific initial activity slightly increases up to 200 mM of methiononitrile. The percent of formed amide increases with the initial nitrile concentration. The purified methiononitrile makes it possible to obtain a better activity and a low percent of amide.

What is claimed is:

1. An isolated and purified DNA segment coding for a polypeptide having nitrilase activity and that hydrolyzes nitriles to carboxylates, wherein said DNA segment is selected from the group consisting of:

a DNA sequence coding for a polypeptide having nitrilase activity and nucleotide sequence SEQ ID NO: 4, as shown in FIG. 4A and 4B, a degenerate of said DNA sequence resulting from the degeneracy of the genetic code, and a DNA molecule that hybridizes with the complement of said DNA sequence under the following conditions:
hybridization buffer: 5×SSC, 5×Denhardt, 0.1% SDS, 50 mM $Na_3PO_4$, pH 6.5, 250 μg/ml of ssDNA; hybridization temperature: 50° C.;
washing conditions: 1 h, 6×SSC, room temperature, and 5 min, 2×SSC, 0.1% SDS, 50° C., and which isolated and purified DNA segment ranges in size from about 4.1 Kilobases to about 1064 bases and which codes for a polypeptide having nitrilase activity that hydrolyzes nitrites to carboxylates;

and that hydrolyzes to a carboxylate, a dinitrile of the formula NC—R—CN in which R is an alkylene group having from 1 to 10 carbon atoms, or a mononitrile preferably belonging to the class of aliphatic sulphurized mononitriles.

2. The DNA segment according to claim 1, being recombinant and having nucleotide sequence SEQ ID NO: 4.

3. Recombinant microorganism transformed to express the DNA segment according to claim 1.

4. Microorganism according to claim 3, wherein said DNA segment is carried in a plasmid containing a selection means.

5. Microorganism consisting of the strain *E. coli* TG1 containing plasmid pXL2148, said strain having the reference G4207 and deposited in the Collection Nationale de Cultures de Microorganismes under No. I-1242.

6. Microorganism transformed with an expression cassette consisting of the DNA segment according to claim 1 and signals ensuring the expression of said DNA segment in the host microorganism.

7. Microorganism according to claim 6, wherein the signals comprise, upstream from said DNA segment, a ribosome binding site and a promoter sequence which are homologous or heterologous with the microorganism which naturally produces the polypeptide produced from said DNA segment.

8. Microorganism according to claim 7, wherein the promotor is the tryptophan operon promoter Ptrp of *E. coli*, the lactose operon promoter Plac of *E. coli*, the phage lambda right promoter PR, the phage lambda left promoter PL or at least one strong promoter of Corynebacterium, Comamonas or Pseudomonas.

9. Microorganism according to claim 7, wherein the ribosome binding site is selected from the phage lambda CII gene or from genes of *E. coli*, Comamonas, Pseudomonas or Corynebacterium.

10. Microorganism according to claim 6, wherein the selection means is a marker conferring antibiotic resistance.

11. Recombinant microorganism according to claim 3, selected from the group of strains consisting of *E. coli*, Comamonas, Corynebacterium, Brevibacterium, Rhodococcus and Pseudomonas.

12. DNA segment according to claim 1, wherein said DNA segment is isolated from a *Comamonas testosteroni* strain.

13. DNA segment according to claim 1, wherein the polypeptide encoded by said DNA segment exhibits nitrilase activity on aliphatic nitriles.

14. DNA segment according to claim 1, wherein the polypeptide encoded by said DNA segment exhibits nitrilase activity on aromatic nitriles.

15. Microorganism according to claim 3, which further expresses an *E. coli* GroE chaperone protein or a homologue of eukaryotic or prokaryotic origin, which chaperone protein assists the folding of said polypeptide having nitrilase activity.

16. Microorganism according to claim 10, which further expresses at least one gene encoding an *E. coli* or a homologue of eukaryotic or prokaryotic origin, which chaperone protein assists the folding of said polypeptide having nitrilase activity.

17. Microorganism according to claim 16, wherein said at least one gene encoding the chaperone protein or homologue thereof is carried by a chromosome or by an extrachromosomal element and wherein said at least one gene is amplified.

18. Microorganism according to claim 16, wherein said at least one gene encoding said chaperone protein or homologue thereof is expressed under the dependence of expression systems homologous or heterologous to said microorganism.

* * * * *